United States Patent
Freytag et al.

(10) Patent No.: US 7,815,902 B2
(45) Date of Patent: Oct. 19, 2010

(54) METHODS AND COMPOSITIONS FOR CANCER THERAPY USING A NOVEL ADENOVIRUS

(75) Inventors: Svend O. Freytag, West Bloomfield, MI (US); Jae Ho Kim, West Bloomfield, MI (US); Ken Barton, Sterling Heights, MI (US); Dell Paielli, Wyandotte, MI (US)

(73) Assignee: Henry Ford Health System, Detroit, MI (US)

( * ) Notice: Subject to any disclaimer, the term of this patent is extended or adjusted under 35 U.S.C. 154(b) by 1166 days.

(21) Appl. No.: 11/342,719

(22) Filed: Jan. 30, 2006

(65) Prior Publication Data
US 2009/0280552 A1    Nov. 12, 2009

Related U.S. Application Data

(63) Continuation-in-part of application No. 10/888,492, filed on Jul. 9, 2004.

(60) Provisional application No. 60/486,219, filed on Jul. 9, 2003.

(51) Int. Cl.
| | |
|---|---|
| A61K 38/43 | (2006.01) |
| C07H 21/04 | (2006.01) |
| C12N 7/00 | (2006.01) |
| C12N 9/12 | (2006.01) |
| C12N 15/38 | (2006.01) |

(52) U.S. Cl. ............... 424/93.1; 424/93.6; 424/94.5; 435/183; 435/194; 435/235.1; 435/320.1; 536/23.1; 536/23.4; 536/23.7; 536/23.72

(58) Field of Classification Search ............... 424/93.1, 424/93.6, 94.5; 435/183, 194, 235.1, 320.1; 536/23.1, 23.4, 23.7, 23.72
See application file for complete search history.

(56) References Cited

U.S. PATENT DOCUMENTS

| 5,877,010 A | 3/1999 | Loeb et al. | |
|---|---|---|---|
| 2002/0028785 A1* | 3/2002 | Wold et al. | 514/44 |

FOREIGN PATENT DOCUMENTS

| WO | WO-01/04282 A2 | 1/2001 |
|---|---|---|
| WO | WO-2005/007109 A2 | 1/2005 |

OTHER PUBLICATIONS

PCT International Search Resort for PCT/US07/02682, 4 pages.

Freytag, et al., *A Novel Three-Pronged Approach To Kill Cancer Cells Selectively: Concomitant Viral, Double Suicide Gene, and Radiotherapy*; Human Gene Therapy; Jun. 10, 1998, vol. 9, pp. 1323-1333.

Rogulski et al., *Double Suicide Gene Therapy Augments The Antitumor Activity Of A Replication-Competent Lytic Adenovirus Through Enchanced Cytotoxicity And Radiosensitization*; Human Gene Therapy; Jan. 1, 2000, vol. 11, No. 1, pp. 67-76.

Freytag et al., *Efficacy And Toxicity Of Replication-Competent Adenovirus-Mediated Double Suidcide Gene Therapy In Combination With Radiation therapy In An Orthotopic Mouse Prostate Cancer Model*; International Journal of Radiation Oncology, Biology and Physics; Nov. 1, 2002, vol. 54, No. 3, pp. 873-885.

Freytag et al., *Phase I Study of Replication-competent Adenovirus-mediated Double Suicide Gene Therapy for the Treatment of Locally Recurrent Prostate Cancer*; Cancer Research; Sep. 1, 2002, vol. 62, No. 17, pp. 4968-4976.

Kievit et al., *Superiority of Yeast over Bacterial Cytosine Deaminase for Enzyme/Prodrug Gene Therapy in Colon Cancer Xenografts*; Cancer Research; Apr. 1, 1999, vol. 59, No. 7, pp. 1417-1421.

Hamstra et al., *Enzyme/Prodrug Therapy for Head and Neck Cancer Using a Catalytically Superior Cytosine Deaminase*; Human Gene Therapy; Aug. 10, 1999, vol. 10, No. 12, pp. 1993-2003.

Kievit et al., *Yeast Cytosine Deaminase Improves Radiosensitization and Bystander Effect by 5-Fluorocytosine of Human Colorectal Caner Xenografts*; Cancer Research; Dec. 1, 2000, vol. 60, No. 23, pp. 6649-6655.

Black et al., *Herpes Simplex Virus-1 Thymidine Kinase Mutants Created by Semi-Random Sequence Mutagenesis Improve Prodrug-mediated Tumor Cell Killing*; Cancer Research; Apr. 1, 2001, vol. 61, No. 7, pp. 3022-3026.

Wiewrodt et al., *Adenovirus-mediated Gene Transfer of Enhanced Herpes Simplex Virus Thymidine Kinase Mutants Improves Prodrug-mediated Tumor Cell Killing*; Cancer Gene Therapy; May 2003, vol. 10, No. 5, pp. 353-364.

Barton et al., *GENIS: Gene Expression of Sodium Iodide Symporter for Noninvasive Imaging of Gene Therapy Vectors and Quantification of Gene Expression* In Vivo. Molecular Therapy; Sep. 2003, vol. 8, No. 3, pp. 508-518.

PCT International Search Report for PCT/US04/22320; 5 pages.

* cited by examiner

*Primary Examiner*—Kevin K. Hill
(74) *Attorney, Agent, or Firm*—Rader, Fishman & Grauer PLLC; James F. Kamp

(57) ABSTRACT

The invention comprises a novel virus that can kill mammalian cancer cells efficiently. The virus produces a novel protein that converts two non-toxic prodrugs into potent chemotherapeutic agents. These chemotherapeutic agents are produced locally and help the virus kill the cancer cells as well as sensitize them to radiation. In preclinical studies, the virus has proven effective at killing a variety of mammalian cancer cells either alone or when combined with prodrug therapy and/or radiation therapy. The invention may provide a safe and effective treatment for human cancer.

4 Claims, 3 Drawing Sheets

METHODS AND COMPOSITIONS FOR CANCER THERAPY USING A NOVEL ADENOVIRUS

CROSS-REFERENCE TO RELATED APPLICATIONS

This application is a continuation-in-part of presently pending U.S. patent application Ser. No. 10/888,492, filed Jul. 9, 2004, entitled "Methods And Compositions For Cancer Therapy Using a Novel Adenovirus," which claims priority to U.S. provisional applications 60/486,219, filed Jul. 9, 2003, both of which are hereby fully incorporated herein by reference.

FIELD OF THE INVENTION

Generally, the present invention relates to a cancer therapy. More specifically, the present invention relates to an adenovirus-based cancer therapy.

BACKGROUND

Despite advances in both diagnosis and therapy, the annual number of cancer related deaths has not decreased during the past 60 years. Although conventional cancer therapies (surgery, radiotherapy, chemotherapy) produce a high rate of cure for patients with early stage disease, many cancers recur and the majority of patients with advanced cancer eventually succumb to the disease. The limitations of conventional cancer therapies do not derive from their inability to ablate tumor, but rather from limits on their ability to do so without excessively damaging the patient. It is this consideration that constrains the extent of surgical resection, the dose of radiation and volume to be irradiated, and the dose and combination of chemotherapeutic drugs. Improving the effectiveness of a treatment is of no clinical value if there is no significant increase in the differential response between tumor and normal tissue (i.e., therapeutic index).

Nonetheless, improved methods and novel agents for treating cancer have resulted in increased survival time and survival rate for patients with various types of cancer. For example, improved surgical and radiotherapeutic procedures result in more effective removal of localized tumors. Surgical methods, however, can be limited due, for example, to the location of a tumor or to dissemination of metastatic tumor cells. Radiotherapy also can be limited by other factors that limit the dose that can be administered. Tumors that are relatively radioresistant will not be cured at such a dose.

Although a single treatment modality such as radiation therapy, chemotherapy, surgery or immunotherapy can result in improvement of a patient, superior results can be achieved when such modalities are used in combination. In particular, treatment with a combination of radiotherapy, which can be directed to a localized area containing a tumor, and chemotherapy or immunotherapy, which provide a systemic mode of treatment, can be useful where dissemination of the disease has occurred or is likely to occur. Unfortunately, the therapeutic usefulness of radiation therapy can be limited where the tumor cells are relatively radioresistant, since the dose is limited by the tolerance of normal tissue in the radiation field. Thus, there exists a need to sensitize cancer tumors to the effects of radiotherapy so that it can more effectively reduce the severity of a tumor in a patient. Further, it would be useful to develop a treatment that more specifically isolates the location of the radiation, thus preventing the effects of radiation treatment on healthy cells.

In related fashion, to mitigate unwanted effects of some chemotherapies, adenovirus vectors have been used to transduce tumor cells with so-called "chemogenes" that convert a nontoxic substance, or "prodrug", into a toxic, therapeutically effective form. Several new approaches involving gene therapy are under consideration for improving the therapeutic index of cancer therapies.

One of these approaches, so-called "suicide gene therapy," involves the transfer and expression of non-mammalian genes encoding enzymes that convert non-toxic prodrugs into toxic anti-metabolites. Two "suicide genes" that are currently being evaluated in clinical trials are the *E. Coli* cytosine deaminase (CD) and herpes simplex virus type-1 thymidine kinase (HSV-1 TK) genes, which confer sensitivity to 5-fluorocytosine (5-FC) and ganciclovir (GCV), respectively. Following targeted transfer of these genes to the tumor, the 5-FC and GCV prodrugs are converted locally into potent chemotherapeutic agents resulting in significant tumor cell death (see reference 1 (and the references cited therein) in the List of References Section below). Thus, the dose-limiting systemic toxicity associated with conventional chemotherapies is mitigated.

Previously, the bacterial CD and wild-type HSV-1 TK genes have been coupled to create a novel CD/HSV-1 TK fusion gene (see reference (hereinafter "ref.") 1 in the List of References Section). The CD/HSV-1 TK fusion gene allows for combined use of CD/5-FC and HSV-1 TK/GCV suicide gene therapies. It has been previously demonstrated that CD/5-FC and HSV-1 TK/GCV suicide gene therapies render malignant cells sensitive to specific pharmacological agents and importantly, sensitize them to radiation (see refs. 1-9). Using a novel, oncolytic, replication-competent adenovirus (Ad5-CD/TKrep) containing the prototype CD/HSV-1 TK fusion gene (ref. 10), the safety and efficacy of replication-competent adenovirus-mediated double suicide gene therapy without and with radiation therapy in several preclinical cancer models (refs. 10-13) and more recently, in human prostate cancer patients (refs. 14 and 15) have been demonstrated.

In these clinical trials targeting human prostate cancer, the Ad5-CD/TKrep virus proved to be safe up to a dose of $10^{12}$ Vp when combined with up to 3 weeks of 5-FC and GCV (vGCV) prodrug therapy without (ref. 14) and with (ref. 15) conventional dose (70 Gy) three dimensional conformal radiation therapy (3DCRT). Moreover, these treatment regimens have demonstrated signs of clinical activity (refs 14 and 15).

Nonetheless, despite these advances, a significant need remains for inventions that comprise effective methods and compositions for use in cancer therapies. The present invention was developed in light of these and other drawbacks.

SUMMARY OF THE INVENTION

The present invention comprises novel, improved methods and compositions for cancer therapy which comprise a novel virus that can kill mammalian cancer cells efficiently. The virus produces a novel protein that converts non-toxic prodrugs into potent chemotherapeutic agents. These chemotherapeutic agents are produced locally and help the virus kill the cancer cells as well as sensitize them to radiation. In preclinical studies, the virus has proven effective at killing a variety of human cancer cells either alone or when combined with prodrug therapy and/or radiation therapy.

The invention comprises a novel, "second-generation" adenovirus (designated "Ad5-yCD/mutTK$_{SR39}$rep-ADP") with at least two significant improvements relative to the previously disclosed prototype Ad5-CD/TKrep virus. Ad5- yCD/mutTK$_{SR39}$rep-ADP contains an improved yCD/mutTK$_{SR39}$ fusion gene whose product is more, efficient at converting the 5-FC and GCV prodrugs into their active chemotherapeutic agents. Moreover, Ad5-yCD/mutTK$_{SR39}$rep-ADP expresses the Ad5 ADP protein, which significantly increases the oncolytic activity of replication-competent adenoviruses. Relative to the prototype Ad5-CDITKrep virus, Ad5-yCD/mutTK$_{SR39}$rep-ADP has demonstrated greater viral oncolytic and chemotherapeutic activity in preclinical cancer models. The data suggest that the Ad5-yCD/mutTK$_{SR39}$rep-ADP virus comprising the present invention will exhibit low toxicity and significant anti-tumor activity clinically when combined with 5-FC and GCV prodrug therapy and radiation therapy.

Other aspects of the invention will be apparent to those skilled in the art after reviewing the drawings and the detailed description below.

BRIEF DESCRIPTION OF THE DRAWINGS

The present invention will now be described, by way of example, with reference to the accompanying drawings, in which.

DETAILED DESCRIPTION OF THE INVENTION

Figure 1:
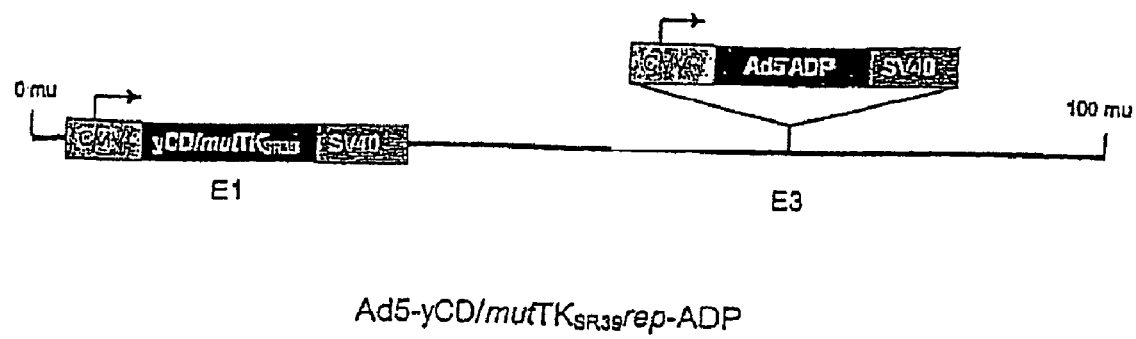
FIG. 1 is a schematic representation of the Ad5-yCD/mutTK$_{SR39}$rep-ADP virus of the present invention.

Generally, the present invention comprises methods and compositions for the treatment for cancer. More specifically, the present invention provides a treatment that, when administered with prodrugs, can kill cancer cells and make the remaining cancer cells more sensitive to radiation.

Embodiments of the present invention include a novel virus that produces a protein that can convert non-toxic prodrugs into chemotherapeutic agents. The prodrugs can be produced locally or administered in conjunction with the treatment. Preferably, the virus is an oncolytic, replication-competent adenovirus such as, but not limited to, Ad5-yCD/mutTK$_{SR39}$rep-ADP. When administered to a patient in need of such treatment, the adenovirus converts at least two prodrugs into chemotherapeutic agents. These prodrugs can include, but are not limited to, 5-fluorocytosine (5-FC) and ganciclovir (GCV and derivatives thereof).

In addition to the ability to convert the prodrugs into chemotherapeutic agents, embodiments of the present invention sensitize the cells to radiation. By sensitizing the cells, lower doses of radiation can be used without limiting the benefits of radiation. Further, the radiation therapy is more effective because the cancer cells are more sensitive to the radiation, while normal cells are not more sensitive, thus limiting the side effects of cancer treatments. The treatment of the present invention can be used in conjunction with other therapies such as surgery, chemotherapy, hormone therapy, and immunotherapy.

In preferred embodiments, the present invention comprises a novel, oncolytic, replication-competent adenovirus (Ad5-yCD/mutTK$_{SR39}$rep-ADP) containing a yeast cytosine deaminase (yCD)/mutant SR39 herpes simplex virus type-1 thymidine kinase (mutTK$_{SR39}$) fusion gene and the adenovirus type 5 (Ad5) adenovirus death protein (ADP) gene. Ad5-yCD/mutTK$_{SR39}$rep-ADP replicates in and kills human cancer cells efficiently. Ad5-yCD/mutTK$_{SR39}$rep-ADP produces a novel yCD/mutTK$_{SR39}$ fusion protein that can convert two prodrugs, 5-fluorocytosine (5-FC) and ganciclovir (GCV; and GCV derivatives), into potent chemotherapeutic agents (referred to as double suicide gene therapy). Both yCD/5-FC and HSV-1 TK$_{SR39}$ suicide gene therapies exhibit potent chemotherapeutic activity and sensitize tumor cells to ionizing radiation.

By way of example only, preclinical studies show that the Ad5-yCD/mutTK$_{SR39}$rep-ADP virus is effective at killing a variety of human cancer cells when used by itself or when combined with double suicide gene therapy and/or radiation therapy. In a clinical setting, the Ad5-yCD/mutTK$_{SR39}$rep-ADP virus could be used as a monotherapy for its virus-mediated oncolytic effect, it could be coupled with yCD/5-FC and HSV-1 Ad5-TK$_{SR39}$/GCV suicide gene therapies for a combined viral oncolytic/chemotherapeutic effect, or it could be coupled with yCD/5-FC and HSV-1 TK$_{SR39}$/GCV suicide gene therapies and radiation therapy for a combined viral oncolytic/chemotherapeutic/radiosensitization effect (referred to as trimodal therapy). Trimodal therapy could be combined with other conventional cancer treatments such as surgery, chemotherapy, hormone therapy and immunotherapy in the management of human cancer.

To develop further this gene therapy-based approach as a cancer treatment, a novel, second-generation adenovirus (Ad5-yCD/mutTK$_{SR39}$rep-ADP) has been developed with two significant improvements relative to the prototype Ad5-CD/TKrep virus. Ad5-yCD/mutTK$_{SR39}$rep-ADP contains an improved yCD/mutTK$_{SR39}$ fusion gene whose product is more efficient at converting the 5-FC and GCV prodrugs into their active chemotherapeutic agents. Moreover, Ad5-yCD/mutTK$_{SR39}$rep-ADP expresses the Ad5 ADP protein, which significantly increases the oncolytic activity of replication-competent adenoviruses. Relative to the prototype Ad5-CDITKrep virus, Ad5-yCD/mutTK$_{SR39}$rep-ADP has demonstrated greater viral oncolytic and chemotherapeutic activity in preclinical cancer models.

Introduction of nucleic acid of the present invention by viral infection offers several advantages over the other listed methods. Higher efficiency can be obtained due to virus' infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Also, additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur.

Features that limit expression to particular cell types can also be included in some embodiments. Such features include, for example, promoter and regulatory elements that are specific for the desired cell type.

In addition, recombinant viral vectors are useful for in vivo expression of the nucleic acids of the present invention because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

The recombinant vector can be administered in several ways. For example, the procedure can take advantage of the target specificity of viral vectors and consequently do not have to be administered locally at the diseased site. However, local administration can provide a quicker and more effective treatment. Administration can also be performed by, for example, intravenous or subcutaneous injection into the subject. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including humans. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Many other such implants, delivery systems, and modules are well known to those skilled in the art.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated.

DEFINITIONS

Unless stated otherwise or suggested by context, the following terms and phrases have the meaning provided below.

The term "gene therapy" as used herein refers to the transfer of genetic material (e.g. DNA or RNA) of interest into a host to treat or prevent a genetic or acquired disease or condition phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. The genetic material of interest can also encode a suicide gene. For a review see, in general, the text "Gene Therapy" (Advances in Pharmacology 40, Academic Press, 1997).

The phrase "in vivo gene therapy" refers to when the genetic material to be transferred is introduced into the target cells of the recipient organism in situ, which is within the recipient. After therapy, the genetically altered target cells express the transfected genetic material in situ. Such therapy also includes repairing the gene in situ, if the host gene is defective.

The phrase "gene expression vehicle" refers to any vehicle capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore, as used herein the expression vehicle may, as needed, not include the 5'UTR and/or 3'UTR of the actual gene to be transferred and only include the specific amino acid coding region. The expression vehicle can include a promoter for controlling transcription of the heterologous material and can be either a constitutive or inducible promoter to allow selective transcription. Enhancers that may be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene.

EXAMPLES

1. Description of the Ad5-yCD/mutTK$_{SR39}$rep-ADP Adenovirus

The complete and partial DNA and translated protein sequences of the Ad5-yCD/mutTK$_{SR39}$rep-ADP adenovirus, yCD/mutTK$_{SR39}$ fusion gene and ADP gene (SEQ ID NOs. 1-5) are disclosed following the List of References Section. The following examples are presented in view of such sequences.

The Ad5-yCD/mutTK$_{SR39}$rep-ADP virus (SEQ ID NO: 1) of the examples is a replication-competent, type 5 adenovirus (the sequence of which is readily known and obtainable to one skilled in the art) that contains an improved yCD/mutTK$_{SR39}$ fusion gene in the E1 region and the Ad5 ADP gene in the E3 region. A schematic representation of Ad5-yCD/mutTK$_{SR39}$rep-ADP is provide in FIG. 1 (in FIG. 1, "CMV"=human cytomegalovirus promoter; "SV40"=simian virus 40 polyadenylation sequences; and "mu"=map units.) As shown in FIG. 1, the CMV-yCD/mutTK$_{SR39}$-SV40 expression cassette is located in the E1 region in place of the deleted 55 kDa E1B gene. The CMV-ADP-SV40 expression cassette is located in the E3 region in place of the deleted E3 genes.

Ad5-yCD/mutTK$_{SR39}$rep-ADP contains a 1,255 base pair (bp) deletion (bases 2,271 to 3,524) in the 55 kDa E1B gene (see SEQ ID NO: 2). Using methods known to those of ordinary skill in the art, two premature translation stop codons were engineered into the 55 kDa E1B gene resulting in the production of a truncated, non-functional, 78 amino acid E1B protein. Ad5-yCD/mutTK$_{SR39}$rep-ADP expresses the wild-type Ad5 E1A and 19 kDa E1B proteins. The yCD/mutTK$_{SR39}$ fusion gene (SEQ ID NO: 4) was inserted in place of the deleted 55 kDa E1B gene. Expression of the yCD/mutTK$_{SR39}$ fusion gene is driven by the human cytomegalovirus (CMV) promoter and utilizes simian virus 40 (SV40) polyadenylation elements. The yCD/mutTK$_{SR39}$ fusion gene codes for a 59 kDa yCD/mutTK$_{SR39}$ fusion protein, which is capable of enzymatically converting 5-fluorocytosine (5-FC) into fluorouracil (5-FU) and ganciclovir (GCV) and its derivatives into their corresponding monophosphates (e.g. GCV-MP). The downstream metabolic products of 5-FU and GCV-MP are potent inhibitors of DNA replication and result in the death of dividing cells. These downstream metabolic products are also potent radiosensitizers and can markedly increase the therapeutic effect of radiation therapy (see refs. 1-14). Cells that express the yCD/mutTK$_{SR39}$ fusion protein, as well as neighboring cells via the bystander effect, are killed by yCD/5-FC and HSV-1 TK$_{SR39}$/GCV suicide gene therapies and are sensitized to the killing effects of ionizing radiation.

Ad5-yCD/mutTK$_{SR39}$rep-ADP also contains a 2.68 kb deletion in the E3 region (bases 28,133 to 30,181), which affects genes that suppress the host immune response but are unnecessary for virus replication (see SEQ ID NO: 3). Ad5-yCD/mutTK$_{SR39}$rep-ADP contains an Ad5 ADP expression cassette in place of the natural Ad5 E3 genes. Expression of the ADP gene (SEQ ID NO: 5) is driven by the human cytomegalovirus (CMV) promoter and utilizes simian virus 40 (SV40) polyadenylation elements. The authentic 11.6 kDa Ad5 ADP protein is produced, which significantly increases the oncolytic activity of replication-competent adenoviruses. Ad5-yCD/mutTK$_{SR39}$rep-ADP lacks all other known Ad5 E3 genes (gp19, 10.4 kDa, 14.5 kDa and 14.7 kDa genes).

2. Construction of the Ad5-yCD/mutTK$_{SR39}$rep-ADP Adenovirus

Plasmids containing adenoviral sequences used in the construction of Ad5-yCD/mutTK$_{SR39}$rep-ADP were obtained from Microbix (Toronto, Canada). To generate the pCMV-yCD/mutTK$_{SR39}$ expression plasmid (left-end vector), the mutant SR39 HSV-1 TK gene (ref. 16) was generated by the polymerase chain reaction (PCR) using linearized pET23d:

HSVTK$_{SR39}$ as template. The following primer pair was used to generate the mutTK$_{SR39}$ PCR product:

(SEQ ID NO: 8)
5'-GATCGGATCCCTCGAGATCGCTAGCATGGCTTCGTACCCCGGC-3

(SEQ ID NO: 9)
5'-GATCGAATTCTTCCGTGTTTCAGTTAGCCTC-3

The resulting 1,128 bp fragment was digested with BamHI (GGATCC)+EcoRI (GAATTC) and cloned between the BamHI+EcoRI sites of pCA14-CDglyTK-E1aE1b (ref. 10) after removal of the prototype CD/HSV-1 TK fusion gene generating pCA14-CMV-mutTK$_{SR39}$-ElaElb. The yCD gene (ref. 17) was generated by PCR using linearized pBAD-ByCD as template. The following primer pair was used to generate the yCD PCR product:

(SEQ ID NO: 10)
5'-GATCCTCGAGCCACCATGGTGACAGGGGGAATG-3'

(SEQ ID NO: 11)
5'-GATCGCTAGCACCTCCCCCACCGCCTCtCCCTCCACCCTCACCAATATCTTC-3'

The resulting 526 bp fragment was digested with XhoI (CTCGAG)+NheI (GCTAGC) and cloned between the XhoI+NheI sites of pCA14-CMV-mutTK$_{SR39}$-E1aE1b generating pCA14-CMV-yCD/mutTK$^{SR39}$E1 aE1b.

To generate pBHG10-PacImod-CMV-ADP (right-end vector), the ADP gene was generated by PCR and cloned between the PacI and SwaI sites of pBHG100-PacImod. pBHG10-PacImod is a derivative of pBHG10 (Microbix; Toronto, Canada) and contains PacI and SwaI sites in the E3 region to facilitate directional cloning.

pBHG10 is a plasmid that contains the entire adenovirus type 5 genome minus bases 188 to 1,339 in the E1 region and bases 28,133 to 30,818 in the E3 region. Using wild-type Ad5 DNA as template, a 333 bp PCR product containing the ADP gene was generated. The following primer pair was used to generate the ADP PCR product:

(SEQ ID NO: 12)
5'-GATCGGATCCCCTGCTCCAGAGATGACCGGC.3'

(SEQ ID NO: 13)
5'-GATCAAGCTTGGAATCATGTCTCAMAATC-3'

The resulting 333 bp PCR product was digested with BamHI (GGATCC)+HindIII (AAGCTT) and cloned into BamHI-HindIII digested pCA14 (Microbix; Toronto, Canada) generating pCA14-ADP. The entire CMV-ADP-SV40 polyA expression cassette was generated by PCR using the following primer pair:

(SEQ ID NO: 14)
5'-GATCATTTAAATAATTCCCTGGCATTATGCCCAGTA-3'

(SEQ ID NO: 15)
5'-GATCTTAATTAATCGATGCTAGACGATCCAGACATG-3'

A SwaI restriction site (ATTTAAAT) was introduced upstream of the CMV promoter in the 5' primer and a PacI restriction site (TTAATTAA) was introduced downstream of the SV40 poly A region with the 3' primer. The PCR product was digested with SwaI and PacI and cloned into SwaI-PacI digested pBGH10-PacImod generating pBGH10-PacImod-CMV-ADP.

To generate Ad5-yCD/mutTK$_{SR39}$rep-ADP virus, pCA14-CMV-yCD/mutTK$_{SR39}$-E1aE1b (10 μg) was linearized by PvuI digestion and co-transfected with ClaI-linearized pBHG10-PacImod-CMV-ADP (30 μg) into HEK 293 cells (Microbix) using the CaP0$_4$-DNA precipitation method. Isolated plaques were harvested 7-14 days later and plaque-purified a second time on HEK 293 cells. Virus form twice purified plaques was used to infect HEK 293 cells to generate crude viral supernatants and CsCl gradient-purified adenovirus.

Figure 2:
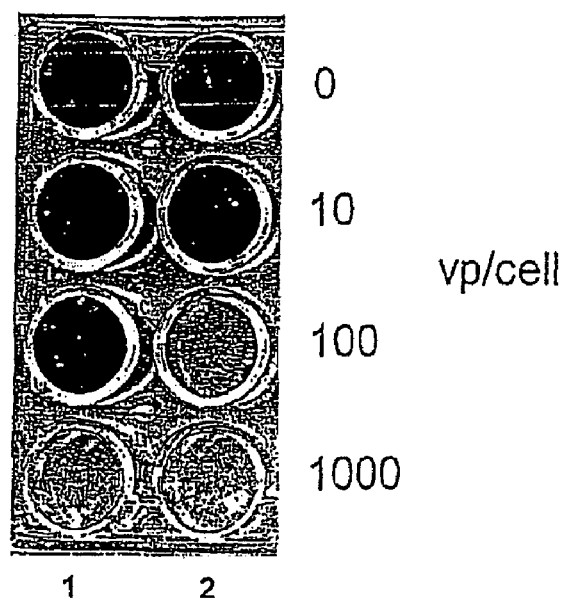
FIG. 2 is a diagram showing an advantage of the ADP gene of the present invention.

3. Advantage of the ADP Gene Contained in Ad5-yCD/mutTK$_{SR39}$rep-ADP In Vitro Human DU145 prostate adenocarcinoma cells were plated in a 24-well plate at a concentration of 5×10$^4$ cells/well and were infected with graded amounts of the Ad5-CD/TKrep (lane 1) and Ad5-yCD/mutTK$_{SR39}$rep-ADP viruses (lane 2). Five days later, cells were fixed and stained with crystal violet. The results (as shown in FIG. 2, "Vp"=viral particles) clearly demonstrate that replication-competent adenoviruses containing the Ad5 ADP gene and expressing the ADP protein (i.e. Ad5-yCD/mutTK$_{SR39}$rep-ADP) possess significantly greater oncolytic activity than adenoviruses that lack ADP. In other words, the presence of the Ad5 ADP gene significantly increased the oncolytic activity of replication competent adenoviruses. These results demonstrate, in vitro, the advantage of the ADP gene contained in Ad5-yCD/mutTK$_{SR39}$rep-ADP.

Figure 3:
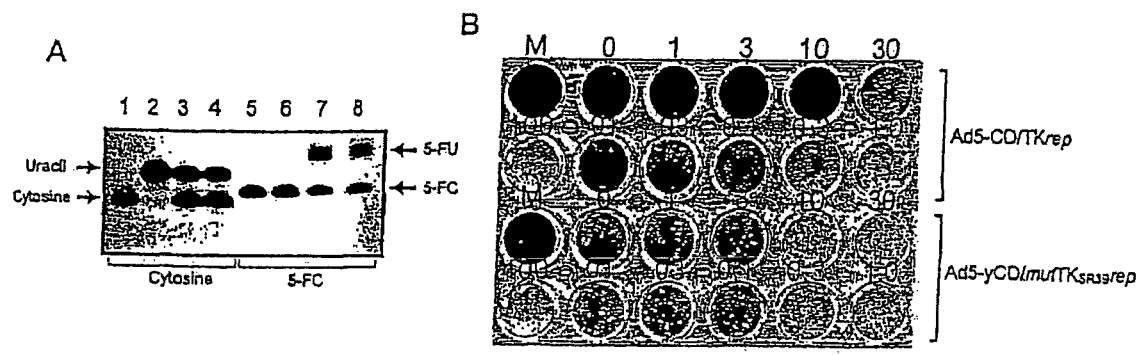
FIGS. 3A and 3B are diagrams showing the advantage of the improved yCD/mutTK$_{SR39}$ gene of the invention.

4. Advantage of the yCD/mutTK$_{SR39}$ Gene Contained in Ad5-yCD/mutTK$_{SR39}$rep-ADP In Vitro A. CD Assays LNCaP C$_{4-2}$ cells were mock-infected (lanes 1 & 5), or infected with Ad5-CD/TKrep (lanes 2 & 6), Ad5-yCD/mutTK$_{SR39}$rep-ADP (lanes 3 & 7), Ad5-yCD/mutTK$_{SR39}$rep-hNIS (lanes 4 & 8) at a MOI of 10. Seventy two hours later, cells were examined for CD activity using [$^{14}$C]-cytosine (lanes 1-4) and [$^3$H]-5-FC (lanes 4-8) as substrates. The results are shown in FIG. 3A [(Cytosine (lower left arrow), uracil (upper left arrow), 5-FC (upper right arrow), 5-FU (lower right arrow)]. As shown by FIG. 3A, recombinant adenoviruses that express the improved yCD/mutTK$_{SR39}$rep gene, such as Ad5-yCD/mutTK$_{SR39}$rep-ADP, demonstrate greater conversion of 5-FC into 5-FU, but not cytosine into uracil, than viruses expressing the CD/HSV-1 TK fusion gene contained in the prototype Ad5-CD/TKrep virus.

B. Cytopathic Effect Assay

Cells (10$^6$ cells, 60 mm dish) were mock-infected or infected with Ad5-CD/TKrep or Ad5-yCD/mutTK$_{SR39}$rep-ADP at an MOI of 3. The next day, cells were replated (24 well plate) in medium containing varying concentrations of 5-FC (wells 3-7 and 15-19, going left to right, top to bottom) or GCV (wells 8-12 and 20'-24, going left to right, top to bottom) in μg/ml. Cells were stained with crystal violet 9 days later. The results (as shown in FIG. 3B) demonstrate that recombinant adenoviruses expressing the improved yCD/mutTKrep gene, such as Ad5-yCD/mutTK$_{SR39}$rep-ADP, achieve greater cell kill when combined with 5-FC prodrug therapy than viruses expressing the CD/HSV-1 TK fusion gene contained in the prototype Ad5-yCD/TKrep virus. Together, the results of FIGS. 3A and 3B show, in vitro, the advantage of the yCD/mutTK$_{SR39}$ gene, which is contained in Ad5-yCD/mutTK$_{SR39}$ rep-ADP.

The results of this example also demonstrate that yCD/5-FC and HSV-1 TK$_{SR39}$/GCV suicide gene therapies can be used to increase the therapeutic effect of the Ad5-yCD/mutTK$_{SR39}$rep-ADP virus itself. Ad5-yCD/mutTK$_{SR39}$rep-ADP contains a novel yCD/mutTK$_{SR39}$ fusion gene whose product has improved catalytic activity relative to the CD/HSV-1 TK fusion protein produced by the prototype Ad5-CD/TKrep virus. Recombinant adenoviruses that express the improved yCD/mutTK$_{SR39}$ fusion protein demonstrate significantly greater conversion of 5-FC into 5-FU, and possibly GCV into GCV-MP, than viruses that express the prototype CD/HSV-1-TK fusion protein. Thus, yCD/5-FC and HSV-1 TK$_{SR39}$/GCV suicide gene therapies can be used independently and together to augment the tumor destructive effects of the Ad5-yCD/mutTK$_{SR39}$rep-ADP virus.

Figure 4:
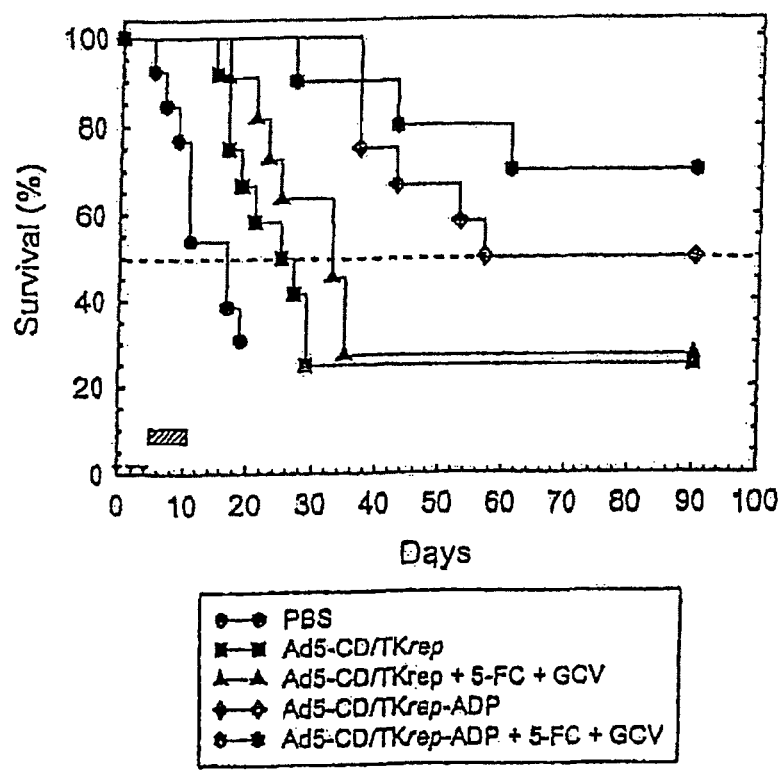
FIG. 4 is a diagram showing an advantage of the ADP gene of the present invention

5. Advantage of the ADP Gene Contained in Ad5-yCD/mutTK$_{SR39}$rep-ADP In Vivo Intramuscular (leg) C33A tumors (150-200 mm$^3$) were injected with 10$^{10}$ vp of Ad5-CD/TKrep or Ad5-CD/TKrep-ADP on Days 0, 2 and 4 (arrowheads in FIG. 4). 5-FC (500 mg/kg/day) and GCV (30 mg/kg/day) were administered on Days 5-11 (hatched bar in FIG. 4). Tumor volume was monitored every other day. The predetermined endpoint was 500 mm$^3$. Survival is defined as an animal having no tumor (cure) or a tumor<500 mm$^3$ on Day 90. The results (as shown in FIG. 4 and Table 1 below) show greater destruction of tumor cells in vivo and thus demonstrate the advantage of the ADP gene, which is contained in Ad5-yCD/mutTK$_{SR39}$rep-ADP. In other words, the presence of the Ad5 ADP gene significantly increased the oncolytic activity of replication competent adenoviruses in vivo as well as in vitro.

6. Effectiveness of Ad5-yCD/mutTK$_{SR39}$rep-ADP In Vivo in Mouse Model

Figure 5:
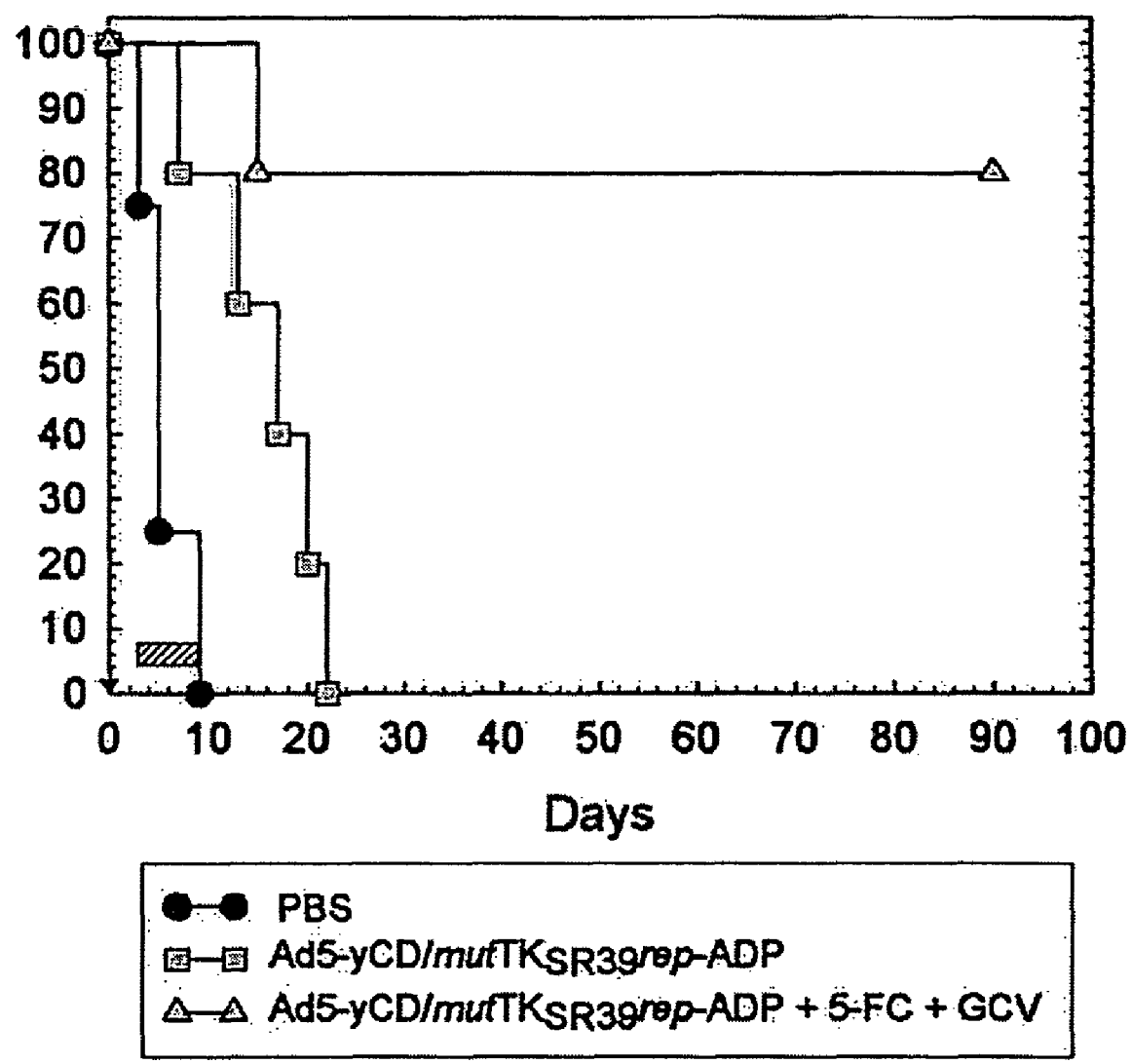
FIG. 5 shows Kaplan-Meier plots with Ad5-yCD/mutTK$_{SR39}$rep-ADP in intraprostatic LNCaP C4-2 mouse model.

Male SCID mice bearing intraprostatic LNCaP C4-2 tumors (~25-50 mm$^3$ in size) were injected with about 10$^9$ vp of Ad5-yCD/mutTK$_{SR39}$rep-ADP on Day 0 (arrowhead in FIG. 5). 5-FC (500 mg/kg/day) and GCV (30 mg/kg/day) were administered on Days 3-9 (hatched bar in FIG. 5). Serum PSA was measured weekly. The predetermined endpoint was PSA=500 ng/ml. The results (as shown in FIG. 5 and Table 2) show an increase in median survival time and/or tumor cure in mouse model using Ad5-yCD/mutTK$_{SR39}$rep-ADP of the present invention.

TABLE 2

Results with Ad5-yCD/mutTK$_{SR39}$rep-ADP in LNCaP C4-2 Tumor Model.

| Group | Median Survival (days) | Tumor cure (%) | P value Log Rank (Survival) | P value Fisher Exact (Tumor Cure) |
|---|---|---|---|---|
| PBS | 5 | 0 (0/8) | | |
| Ad5-yCD/mutTK$_{SR39}$rep-ADP | 17 | 0 (0/11) | .038[a] | NA[a] |
| Ad5-yCD/mutTK$_{SR39}$rep-ADP + 5-FC + GCV | >90 | 80 (8/10) | <0.001[b] | <0.001[b] |

[a]Ad5-yCD/mutTK$_{SR39}$rep-ADP vs. PBS;
[b]Ad5-yCD/mutTK$_{SR39}$rep-ADP + 5-FC + GCV vs. PBS.

7. Radiosensitized Human Cancer Cells using yCD/5-FC and HSV-1 TK$_{SR39}$/GCV As shown in previous experiments by the inventors (see refs. 1-14), yCD/5-FC and HSV-1 TK$_{SR39}$/GCV suicide gene therapies can also be used to radiosensitize human cancer cells. Ad5-yCD/mutTK$_{SR39}$rep-ADP contains a novel yCD/mutTK$_{SR39}$ fusion gene whose product has improved catalytic activity relative to the CD/HSV-1 TK fusion protein produced by the prototype Ad5-CD/TKrep virus. The previous studies demonstrated that CD/5-FC and HSV-1 TK/GCV suicide gene therapies can sensitize human tumor cells to ionizing radiation. Thus, since Ad5-yCD/mutTK$_{SR39}$ rep-ADP expresses an improved yCD/mutTK$_{SR39}$ fusion protein, it may result in greater tumor cell radiosensitization in vivo.

TABLE 1

Summary of Results with Ad5-CD/TKrep-ADP in C33A Tumor Model.

| Group | Median Survival | Tumor Care (%) | Pvalue Log Rank (Survival) | Pvalue Fisher Exact (Tumor Cure) |
|---|---|---|---|---|
| PBS | 17 | 0(0/13) | | |
| Ad5-CD/TKrep | 26 | 0(0/12) | | |
| Ad5-CD/TKrep + 5-FC + GCV | 33 | 9(1/11) | | |
| Ad5-CD/TKrep-ADP | >90 | 8(1/12) | 0.022[b] | 1.000[b] |
| Ad5-CD/TKrep-ADP + 5-FC + GCV | >90 | 70(7/10) | 0.026[c] | .008[c] |

[a]Median survival is in days.
[b]Ad5-CD/TKrep-ADP vs. Ad5-CD/TKrep
[c]Ad5-CD/TKrep-ADP + 5-FC + GCV vs. Ad5-CD/TKrep + 5-FC + GCV Throughout this application, various references are noted by reference numbers. A numbered list of these references with their full citations is provided below. The disclosures of these references in their entireties are hereby incorporated by reference into this application in order to more fully describe the state of the art to which this invention pertains.

While the present invention has been particularly shown and described with reference to the foregoing preferred and alternative embodiments, and examples, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and composition within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

LIST OF REFERENCES

1. Rogulski, K. R., Kim, J. H., Kim, S. H., and Freytag, S. O. Glioma cells transduced with an *E. coli* CD/HSV-1 TK fusion gene exhibit enhanced metabolic suicide and radiosensitivity. *Hum. Gene Ther.*, 8: 73-85, 1997.
2. Kim, J. H., Kim, S. H., Brown, S. L., and Freytag, S. O, Selective enhancement by an antiviral agent of the radiation-induced cell killing of human glioma cells transduced with HSV-tk gene. *Cancer Res.*, 54: 6003-6056, 1994.
3. Kim, J. H., Kim, S. H., Kolozsvary, A., Brown, S. L., Kim, O. B., and Freytag, S. O. Selective enhancement of radiation response of herpes simplex virus thymidine kinase transduced 9L gliosarcoma cells in vitro and in vivo by antiviral agents. *Int. J. Radiat. Oncol. Biol. Phys.*, 33: 861-868,1995.
4. Khil, M., Kim, J. H., Mullen, C. A., Kim, S. H., and Freytag, S. O. Radiosensitization' by 5-fluorocytosine of human colorectal carcinoma cells in culture transduced with cytosine deaminase gene. *Clin. Cancer Res.*, 2: 53-57, 1996.
5. Kim, S. H., Kim, J. H., Kolozsvary, A., Brown, S. L., and Freytag, S. O. Preferential radiosensitization of 9L glioma cells transduced with HSV-TK gene by acyclovir. *J. Neurooncol.*, 33: 189-194,1997.
6. Gable, M., Kim, J. H., Kolozsvary, A., Khil, M., and Freytag, S. O, Selective in vivo radiosensitization by 5-fluorocytosine of human colorectal carcinoma cells transduced with the *E. coli* cytosine deaminase gene. *Int. J. Radiat. Oncol. Biol. Phys.*, 41: 883-887, 1998.
7. Rogulski, K. R., Zhang, K., Kolozsvary, A., Kim, J. H., and Freytag, S. O. Pronounced antitumor effects and tumor radiosensitization of double suicide gene therapy. *Clin. Cancer Res.*, 3: 2081-2088, 1997.
8. Kim, J. H., Kolozsvary, A., Rogulski, K. R., Khil, M., and Freytag, S. O, Selective radiosensitization of 9L glioma. in the brain transduced with double suicide fusion gene. *Can. J. Scient Am.* 4:364-369, 1998.
9. Xie, Y., Gilbert, J. D., Kim, J. H., and Freytag, S. O. Efficacy of adenovirus-mediated CD/5-FC and HSV-1TK/GCV suicide gene therapies concomitant with p53 gene therapy. *Clin. Cancer Res.*, 5: 4224-4232, 1999.
10. Freytag, S. O., Rogulski, K. R., Paielli, D. L., Gilbert, J. D., and Kim, J. H. A novel three-pronged approach to selectively kill cancer cells: concomitant viral, double suicide gene, and radiotherapy. *Hum. Gene Ther.*, 9: 1323-1333, 1998.
11. Rogulski, K. R., Wing, M., Paielll, D. L., Gilbert, J. D., Kim, J. H., and Freytag, S. O. Double suicide gene therapy augments the antitumor activity of a replication-competent lytic adenovirus through enhanced cytotoxicity and radiosensitization. *Hum. Gene Ther.*, 11: 67-76, 2000.
12. Paielli, D. L., Wing, M., Rogulski, K. R., Gilbert, J. D., Kolozsvary, A., Kim, J. H., Hughes, J. V., Schnell, M., Thompson, T., and Freytag S. O. Evaluation of the biodistribution, toxicity, and potential of germ line transmission of a replication-competent human adenovirus following intraprostatic administration in the mouse. *Molecular Ther.* 1: 263-274, 2000.
13. Freytag, S. O., Paielli, D., Wing, M., Rogulski, K., Brown, S., Kolozsvary, A., Seely, J., Barton, K., Dragovic, A., and Kim, J. H. Efficacy and toxicity of replication-competent adenovirus-mediated double suicide gene therapy in combination with radiation therapy in an orthotopic mouse prostate cancer model. *Int. J. Radiat. Oncol. Biol. Phys.*, 54: 873-886, 2002.
14. Freytag, S. O., Khil, M., Stricker, H., Peabody, J., Menon, M., DePeralta-Venturina, M., Nafziger, D., Pegg, J., Paielli, D., Brown, S., Barton, K., Lu, M., Aguilar-Cordova, E., and Kim, J. H. Phase I study of replication-competent adenovirus-mediated double suicide gene therapy for the treatment of locally recurrent prostate cancer. *Cancer Res.*, 62: 4968-4976, 2002.
15. Freytag, S. O., Stricker, H., Peabody, J., Menon, M., DePeralta-Venturina, M., Pegg, J., Paiellii, D., Brown, S., Lu, M., and Kim, J. H. Phase I study of replication-competent-adenovirus-mediated double suicide gene therapy in combination with conventional dose three-dimensional conformal radiation therapy for the treatment of locally aggressive prostate cancer. In preparation, 2003.
16. Black, M., Kokoris, M., and Sabo, P. Herpes simplex virus-1 thymidine kinase mutants created by semi-random sequence mutagenesis improve prodrug-mediated tumor cell killing. *Cancer Res.*, 61: 3022-3026, 2001.
17. Kievit, E., Bershad, E., Ng, E., Sethna, P., Dev, I., Lawrence, T., Rehemtulla, A. Superiority of yeast over bactedal cytosine deaminase for enzyme/prodrug gene therapy in colon cancer xenografts. *Cancer Res.*, 59: 1417-1421, 1999.
18. Bischoff J R, Kim D H, Williams A, Heise C, Horn S, Muna M, et al. An adenovirus mutant that replicates selectively in p53-deficient human tumor cells. *Science*, 274: 373-376, 1996.
19. Heise C, Sampson-Johannes A, Williams A, McCormick F von-HoffpD, Ki D H. ONYX-015, an E1B gene-attenuated adenovirus, causes tumor-specific cytolysis and antitumoral efficacy that can be augmented by standard chemotherapeutic agents. *Nature Med.* 3: 639-645, 1997.
20. Ganly, I., Kim, D., Eckhardt, S., Rodriguez, G., Soutar, D., Otto, R., Robertson, A., Park, 0., Gulley, M., Heise, C., von Hoff, D., and Kaye, S. A phase I study of ONYX-015, an E1B attenuated adenovirus, administered intratumorally to patents with recurrent head and neck cancer. *Clin. Cancer Res.*, 6: 798-806, 2000.

21. Nemunaitis, J., Khuri, F., Ganly, I., Arseneau, J., Posner, M., Vokes, E., Kuhn, J., McCarty, T., Landers, S., Blackburn, A., Romel, L., Randlev, B., Kaye, S., and Kim, D. Phase II trial of intratumoral administration of ONYX-015, a replication-selective adenovirus, in patients with refractory head and neck cancer. *J. Clin. Oncol.*, 19: 289-298, 2001.

22. Nemunaitis, J., Ganly, I., Khuri, F., Arsenead, J, Kuhn, J., McCarty, T., Landers, S., Maples, P., Romel, L., Randlev, B., Reid, T., Kaye, S., and Kim, D. Selective replication and oncolysis in p53 mutant tumors with ONYX-015, an E1B-55 kD gene-deleted adenovirus, in patients with advanced head and neck cancer: a phase II trial. *Cancer Res.*, 60: 6359-6366, 2000.

23. Khuri, F., Nemunaitis, J., Ganly, I., Arseneau, J., Tannock, I., Romel., L., Gore, M., Ironside, J., MacDougall, R., Heise, C., Randlev, B., Gillenwater, A., Bruso, P., Kaye, S., Hong, W., and Kim, D. A controlled trial of intratumoral ONYX-015, a selectively-replicating adenovirus, in combination with cisplatin and 5-fluorouracil in patients with recurrent head and neck cancer. *Nature Med.*, 6: 879-885, 2000.

24. Mulvihill, S, Warren, R., Venook, A., Adler, A., Randlev, B., Heise, C., and Kim, D. Safety and feasibility of injection with an E1B-55 kDa gene-deleted, replication-selective adenovirus (ONYX-015) into primary carcinomas of the pancreas: a phase I trial. *Gene Ther.*, 8: 308-315, 2001.

25. Reid, T., Galanis, E., Abbruzzese, J., Sze, D., Andrews, J., Romel, L., Hatfield, M., Rubin, J., and Kim, D. Intra-arterial administration of a replication-selective adenovirus (dl1520) in patients with colorectal carcinoma metastatic to the liver: a phase I trial. *Gene Ther.*, 8: 1618-1626, 2001.

26. Vasey, P., Shulman, L., Campos, S., Davis, J., Gore, M., Johnston, S., Kim, D., O'Neill, V., Siddiqui, N., Seiden, M., and Kaye, S. Phase I trial of intraperitoneal injection of the E1B-55-kd-gene-deleted adenovirus ONYX-015 (dl520) given on days 1 through 5 every 3 weeks in patients with recurrent/refractory epithelial ovarian cancer. *J. Clin. Oncol*, 20: 1562-1569, 2002.

27. Rodriquez, R., Schuur, E., Lim, H., Henderson, G., Simons, J., and Henderson, D. Prostate attenuated replication competent adenovirus (ARCA) CN706: a selective cytotoxic for prostate-specific antigen-positive prostate cancer cells. *Cancer Res.*, 57: 2559-2563, 1997.

28. Chen, Y., DeWeese, T., Dilley, J., Zhang, Y., Li, Y., Ramesh, N., Lee, J., Pennathur-Das, R., Radzyminski, J., Wypych, J., Brignetti, D., Scott, S., Stephens, J., Karpf, D., Henderson, D. and Yu, D. CV706, a prostate cancer-specific adenovirus variant, in combination with radiotherapy produces synergistic antitumor efficacy without increasing toxicity. *Cancer Res.*, 61: 5453-5460, 2001.

29. DeWeese, T., van der Poel, H., Li, S., Mikhak, B., Drew, R., Goemann, M., Hamper, U., DeJong, R., Detorie, N., Roddguez, R., Haulk, T., DeMarzo, A., Piantadosi, S., Yu, D., Chen, Y., Henderson, D., Carducci, M., Nelson, W., and Simons, J. A phase I trial of CV706, a replication-competent, PSA selective oncolytic adenovirus, for the treatment of locally recurrent prostate cancer following radiation therapy. *Cancer Res.*, 61: 7464-7472, 2001.

30. Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251-270 (1991).

31. Capecchi, "Altering the genome by homologous recombination" *Science* 244:1288-1292 (1989).

32. Davies et al., "Targeted alterations in yeast artificial chromosomes for inter-species gene transfer", *Nucleic Acids Research*, Vol. 20, No. 11, pp. 2693-2698 (1992).

33. Dickinson et al., "High frequency gene targeting using insertional vectors", *Human Molecular Genetics*, Vol. 2, No. 8, pp. 1299-1202 (1993).

34. Duff and Lincoln, "Insertion of a pathogenic mutation into a yeast artificial chromosome containing the human APP gene and expression in ES cells", *Research Advances in Alzheimers Disease and Related Disorders*, 1995.

35. Huxley et al., "The human, HPRT gene on a yeast artificial chromosome is functional when transferred to mouse cells by cell fusion", *Genomics*, 9:742-750 (1991).

36. Jakobovits et al., "Germ-line transmission and expression of a human-derived yeast artificial chromosome", *Nature*, Vol. 362, pp. 255-261 (1993).

37. Lamb et al., "Introduction and expression of the 400 kilobase precursor amyloid protein gene in transgenic mice", *Nature Genetics*, Vol. 5, pp. 22-29 (1993).

38. Pearson and Choi, *Expression of the human b-amyloid precursor protein gene from a yeast artificial chromosome in transgenic mice*. Proc. Natl. Acad. Sci. USA, 1993. 90, 10578-82.

39. Rothstein, "Targeting, disruption, replacement, and allele rescue: integrative DNA transformation in yeast" in *Methods in Enzymology*, Vol. 194, "Guide to Yeast Genetics and Molecular Biology", eds. C., Guthrie and G. Fink, Academic Press, Inc., Chap. 19, pp. 281-301 (1991).

40. Schedl et al., "A yeast artificial chromosome covering the tyrosinase gene confers copy number-dependent expression in transgenic mice", *Nature*, Vol. 362, pp. 258-261 (1993).

41. Strauss et al., "Germ line transmission of a yeast artificial chromosome spanning the murine a (1) collagen locus", *Science*, Vol. 259, pp. 1904-1907 (1993).

42. Gilboa, E, Eglitis, M A, Kantoff, P W, Anderson, W F: Transfer and expression of cloned genes using retroviral vectors. BioTechniques 4(6):504-512, 1986.

43. Cregg J M, Vedvick T S, Raschke W C: Recent Advances in the Expression of Foreign Genes in *Pichia pastoris, Bio/Technology* 11:905-910, 1993.

44. Culver, 1998. Site-Directed recombination for repair of mutations in the human ADA gene. (Abstract) Antisense DNA & RNA based therapeutics, February, 1998, Coronado, Calif.

45. Huston et al, 1991 "Protein engineering of single-chain Fv analogs and fusion proteins" in Methods in Enzymology (J J Langone, ed.; Academic Press, New York, N.Y.) 203:46-88.

46. Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203:88-99.

47. Memaugh and Memaugh, 1995 "An overview of phage-displayed recombinant antibodies" in Molecular Methods In Plant Pathology (R P Singh and US Singh, eds.; CRC Press Inc., Boca Raton, Fla.) pp. 359-365.

What is claimed is:

1. An isolated polynucleotide comprising the nucleotide sequence of SEQ ID NO: 4.

2. A recombinant adenovirus comprising an isolated polynucleotide comprising the nucleotide sequence of SEQ ID NO: 5.

3. An isolated polypeptide comprising the amino acid sequence of SEQ ID NO: 6.

4. A recombinant adenovirus comprising an isolated polynucleotide comprising the nucleotide sequence of SEQ ID NO: 1.

* * * * *

SEQUENCE LISTING

<160> NUMBER OF SEQ ID NOS: 15

<210> SEQ ID NO 1
<211> LENGTH: 35180
<212> TYPE: DNA
<213> ORGANISM: Adenovirus

<400> SEQUENCE: 1

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tctctagcat cgaagatcca     360
tttgtctagg gccgcgggga ctttgaccgt ttacgtggag actcgcccag gtgttttcct     420
caggtgtttt ccgcgttccg ggtcaaagtt ggcgttttat tattatagtc agctgacgtg     480
tagtgtattt atacccggtg agttcctcaa gaggccactc ttgagtgcca gcgagtagag     540
ttttctcctc cgagccgctc cgacaccggg actgaaaatg agacatatta tctgccacgg     600
aggtgttatt accgaagaaa tggccgccag tcttttggac cagctgatcg aagaggtact     660
ggctgataat cttccacctc ctagccattt tgaaccacct acccttcacg aactgtatga     720
tttagacgtg acggcccccg aagatcccaa cgaggaggcg gcttcgcaga ttttccccga     780
ctctgtaatg ttggcggtgc aggaagggat tgacttactc acttttccgc cggcgcccgg     840
ttctccggag ccgcctcacc tttcccggca gcccgagcag ccggagcaga gagccttggg     900
tccggtttct atgccaaacc ttgtaccgga ggtgatcgat cttacctgcc acgaggctgg     960
cttttccaccc agtgacgacg aggatgaaga gggtgaggag tttgtgttag attatgtgga    1020
gcacccgggg cacggttgca ggtcttgtca ttatcaccgg aggaatacgg gggacccaga    1080
tattatgtgt tcgcttttgct atatgaggac ctgtggcatg tttgtctaca gtaagtgaaa    1140
attatgggca gtgggtgata gagtggtggg tttggtgtgg taattttttt tttaattttt    1200
acagttttgt ggtttaaaga attttgtatt gtgatttttt taaaaggtcc tgtgtctgaa    1260
cctgagcctg agcccgagcc agaaccggag cctgcaagac ctaccgccg tcctaaaatg     1320
gcgcctgcta tcctgagacg cccgacatca cctgtgtcta gagaatgcaa tagtagtacg    1380
gatagctgtg actccggtcc ttctaacaca cctcctgaga tacacccggt ggtcccgctg    1440
tgccccatta aaccagttgc cgtgagagtt ggtgggcgtc gccaggctgt ggaatgtatc    1500
gaggacttgc ttaacgagcc tgggcaacct ttggacttga gctgtaaacg ccccaggcca    1560
taaggtgtaa acctgtgatt gcgtgtgtgg ttaacgcctt tgtttgctga atgagttgat    1620
gtaagtttaa taaagggtga gataatgttt aacttgcatg gcgtgttaaa tggggcgggg    1680
cttaaagggt atataatgcg ccgtgggcta atcttggtta catctgacct catgaggct     1740
tgggagtgtt tggaagattt ttctgctgtg cgtaacttgc tggaacagag ctctaacagt    1800
acctcttggt tttggaggtt tctgtgggc tcatcccagg caaagttagt ctgcagaatt    1860
aaggaggatt acaagtggga atttgaagag cttttgaaat cctgtggtga gctgtttgat    1920
tctttgaatc tgggtcacca ggcgcttttc caagagaagg tcatcaagac tttgatttt     1980
tccacaccgg ggcgcgctgc ggctgctgtt gcttttttga gttttataaa ggataaatgg    2040
```

```
agcgaagaaa cccatctgag cggggggtac ctgctggatt ttctggccat gcatctgtgg    2100
agagcggttg tgagacacaa gaatcgcctg ctactgttgt cttccgtccg cccggcgata    2160
ataccgacgg aggagcagca gcagcagcag gaggaagcca ggcggcggcg gcaggagcag    2220
agcccatgga acccgagagc cggcctggac cctcgggaat gaatgttgta taggtggctt    2280
aactgtatag atctaattcc ctggcattat gcccagtaca tgaccttatg ggactttcct    2340
acttggcagt acatctacgt attagtcatc gctattacca tggtgatgcg gttttggcag    2400
tacatcaatg ggcgtggata gcggtttgac tcacggggga ttccaagtct ccaccccatt    2460
gacgtcaatg ggagtttgtt ttggcaccaa aatcaacggg actttccaaa atgtcgtaac    2520
aactccgccc cattgacgca aatgggcggt aggcgtgtac ggtgggaggt ctatataagc    2580
agagctcgtt tagtgaaccg tcagatcgcc tggagacgcc atccacgctg ttttgacctc    2640
catagaagac accgggaccg atccagcctg gggatcttcg agtcgaggga tccctcgagc    2700
caccatggtg acaggggaa tggcaagcaa gtgggatcag aagggtatgg acgttgccta    2760
tgaggaggcg gccttaggtt acaaagaggg tggtgttcct attggcggat gtcttatcaa    2820
taacaaagac ggaagtgttc tcggtcgtgg tcacaacatg agatttcaaa agggatccgc    2880
cacactacat ggtgagatct ccactttgga aaactgtggg agattagagg caaagtgta    2940 caaagatacc actttgtata cgacgctgtc tccatgcgac atgtgtacag gtgccatcat    3000
catgtatggt attccacgct gtgttgtcgg tgagaacgtt aatttcaaaa gtaagggcga    3060
gaaatattta caaactagag gtcacgaagt tgttgttgtt gacgatgaga ggtgtaaaaa    3120
gatcatgaaa caatttatcg atgaaagacc tcaggattgg tttgaagata ttggtgaggg    3180 tggagggga ggcggtgggg gaggtgctag catggcttcg tacccgcc atcaacacgc       3240 gtctgcgttc gaccaggctg cgcgttctcg cggccatagc aaccgacgta cggcgttgcg    3300
ccctcgccgg cagcaagaag ccacggaagt ccgcccggag cagaaaatgc ccacgctact    3360
gcgggtttat atagacggtc cccacgggat ggggaaaacc accaccacgc aactgctggt    3420
ggccctgggt tcgcgcgacg atatcgtcta cgtacccgag ccgatgactt actggcgggt    3480
gctgggggct tccgagacaa tcgcgaacat ctacaccaca caacaccgcc tcgaccaggg    3540
tgagatatcg gccgggacg cggcggtggt aatgacaagc gcccagataa caatgggcat    3600
gccttatgcc gtgaccgacg ccgttctggc tcctcatatc ggggggagg ctgggagctc     3660 acatgccccg ccccccggcc tcaccatctt cctcgaccgc catcccatcg ccttcatgct    3720
gtgctacccg gccgcgcggt accttatggg cagcatgacc ccccaggccg tgctggcgtt    3780 cgtgccctc atcccgccga ccttgccggg caccaacatc gtgcttgggg cccttccgga    3840
ggacagacac atcgaccgcc tggccaaacg ccagcgcccc ggcgagcggc tggacctggc    3900
tatgctggct gcgattcgcc gcgtttacgg gctacttgcc aatacggtgc ggtatctgca    3960
gtgcggcggg tcgtggcggg aggactgggg acagctttcg gggacggccg tgccgcccca    4020
gggtgccgag cccagagca acgcgggccc acgacccat atcggggaca cgttatttac      4080
cctgtttcgg gcccccgagt tgctggcccc caacggcgac ctgtataacg tgtttgcctg    4140
ggccttggac gtcttggcca acgcctccg ttccatgcac gtctttatcc tggattacga     4200
ccaatcgccc gccggctgcc gggacgccct gctgcaactt acctccggga tggtccagac    4260
ccacgtcacc acccccggct ccataccgac gatatgcgac ctggcgcgca cgtttgcccg    4320
ggagatgggg gaggctaact gaaacacgga agaattcaag cttgtcgact tcgagcaact    4380
```

```
tgtttattgc agcttataat ggttacaaat aaagcaatag catcacaaat ttcacaaata    4440
aagcattttt ttcactgcat tctagttgtg gtttgtccaa actcatcaat gtatcttatc    4500
atgtctggat cgtctagcat cgaagatctg gatctgggcg tggttaaggg tgggaaagaa    4560
tatataaggt gggggtctta tgtagttttg tatctgtttt gcagcagccg ccgccgccat    4620
gagcaccaac tcgtttgatg gaagcattgt gagctcatat ttgacaacgc gcatgccccc    4680
atgggccggg gtgcgtcaga atgtgatggg ctccagcatt gatggtcgcc ccgtcctgcc    4740
cgcaaactct actaccttga cctacgagac cgtgtctgga acgccgttgg agactgcagc    4800
ctccgccgcc gcttcagccg ctgcagccac cgcccgcggg attgtgactg actttgcttt    4860
cctgagcccg cttgcaagca gtgcagcttc ccgttcatcc gcccgcgatg acaagttgac    4920
ggctcttttg gcacaattgg attctttgac ccgggaactt aatgtcgttt ctcagcagct    4980
gttggatctg cgccagcagg tttctgccct gaaggcttcc tcccctccca atgcggttta    5040
aaacataaat aaaaaaccag actctgtttg gatttggatc aagcaagtgt cttgctgtct    5100
ttatttaggg gttttgcgcg cgcggtaggc ccgggaccag cggtctcggt cgttgagggt    5160
cctgtgtatt ttttccagga cgtggtaaag gtgactctgg atgttcagat acatgggcat    5220
aagcccgtct ctggggtgga ggtagcacca ctgcagagct tcatgctgcg gggtggtgtt    5280
gtagatgatc cagtcgtagc aggagcgctg ggcgtggtgc ctaaaaatgt ctttcagtag    5340
caagctgatt gccaggggca ggcccttggt gtaagtgttt acaaagcggt taagctggga    5400
tgggtgcata cgtggggata tgagatgcat cttggactgt attttttaggt tggctatgtt    5460 cccagccata tccctccggg gattcatgtt gtgcagaacc accagcacag tgtatccggt    5520
gcacttggga aatttgtcat gtagcttaga aggaaatgcg tggaagaact tggagacgcc    5580
cttgtgacct ccaagatttt ccatgcattc gtccataatg atggcaatgg gcccacgggc    5640
ggcggcctgg gcgaagatat ttctgggatc actaacgtca tagttgtgtt ccaggatgag    5700
atcgtcatag gccatttta caaagcgcgg gcggagggtg ccagactgcg gtataatggt    5760
tccatccggc ccaggggcgt agttaccctc acagatttgc atttcccacg ctttgagttc    5820
agatgggggg atcatgtcta cctgcggggc gatgaagaaa acggtttccg gggtagggga    5880
gatcagctgg gaagaaagca ggttcctgag cagctgcgac ttaccgcagc cggtgggccc    5940
gtaaatcaca cctattaccg gctgcaactg gtagttaaga gagctgcagc tgccgtcatc    6000
cctgagcagg ggggccactt cgttaagcat gtccctgact cgcatgtttt ccctgaccaa    6060
atccgccaga aggcgctcgc cgcccagcga tagcagttct tgcaaggaag caaagttttt    6120
caacggtttg agaccgtccg ccgtaggcat gcttttgagc gtttgaccaa gcagttccag    6180
gcggtcccac agctcggtca cctgctctac ggcatctcga tccagcatat ctcctcgttt    6240
cgcgggttgg ggcggctttc gctgtacggc agtagtcggt gctcgtccag acgggccagg    6300
gtcatgtctt tccacgggcg cagggtcctc gtcagcgtag tctgggtcac ggtgaagggg    6360
tgcgctccgg gctgcgcgct ggccagggtg cgcttgaggc tggtcctgct ggtgctgaag    6420
cgctgccggt cttcgccctg cgcgtcgcc aggtagcatt tgaccatggt gtcatagtcc    6480
agcccctccg cggcgtggcc cttggcgcgc agcttgccct ggaggaggc gccgcacgag    6540 gggcagtgca gacttttgag ggcgtagagc ttgggcgcga gaaataccga ttccggggag    6600
taggcatccg cgccgcaggc cccgcagacg gtctcgcatt ccacgagcca ggtgagctct    6660
ggccgttcgg ggtcaaaaac caggtttccc ccatgctttt tgatgcgttt cttacctctg    6720
gtttccatga gccggtgtcc acgctcggtg acgaaaaggc tgtccgtgtc cccgtataca    6780
```

```
gacttgagag gcctgtcctc gagcggtgtt ccgcggtcct cctcgtatag aaactcggac   6840
cactctgaga caaaggctcg cgtccaggcc agcacgaagg aggctaagtg ggaggggtag   6900
cggtcgttgt ccactagggg gtccactcgc tccagggtgt gaagacacat gtcgccctct   6960
tcggcatcaa ggaaggtgat tggtttgtag gtgtaggcca cgtgaccggg tgttcctgaa   7020 gggggctat  aaaaggggt  gggggcgcgt tcgtcctcac tctcttccgc atcgctgtct   7080
gcgagggcca gctgttgggg tgagtactcc ctctgaaaag cgggcatgac ttctgcgcta   7140
agattgtcag tttccaaaaa cgaggaggat ttgatattca cctggcccgc ggtgatgcct   7200
ttgagggtgg ccgcatccat ctggtcagaa aagacaatct ttttgttgtc aagcttggtg   7260
gcaaacgacc cgtagagggc gttggacagc aacttggcga tggagcgcag ggtttggttt   7320
ttgtcgcgat cggcgcgctc cttggccgcg atgtttagct gcacgtattc gcgcgcaacg   7380
caccgccatt cggaaagac  ggtggtgcgc tcgtcgggca ccaggtgcac gcgccaaccg   7440
cggttgtgca gggtgacaag gtcaacgctg gtggctacct ctccgcgtag gcgctcgttg   7500
gtccagcaga ggcggccgcc cttgcgcgag cagaatggcg gtaggggtc  tagctgcgtc   7560 tcgtccgggg ggtctgcgtc cacggtaaag accccgggca gcaggcgcgc gtcgaagtag   7620
tctatcttgc atccttgcaa gtctagcgcc tgctgccatg cgcgggcggc aagcgcgcgc   7680
tcgtatgggt tgagtggggg accccatggc atggggtggg tgagcgcgga ggcgtacatg   7740
ccgcaaatgt cgtaaacgta gaggggctct ctgagtattc caagatatgt agggtagcat   7800
cttccaccgc ggatgctggc gcgcacgtaa tcgtatagtt cgtgcgaggg agcgaggagg   7860
tcgggaccga ggttgctacg ggcgggctgc tctgctcgga agactatctg cctgaagatg   7920
gcatgtgagt tggatgatat ggttggacgc tggaagacgt tgaagctggc gtctgtgaga   7980
cctaccgcgt cacgcacgaa ggaggcgtag gagtcgcgca gcttgttgac cagctcggcg   8040
gtgacctgca cgtctagggc gcagtagtcc agggtttcct tgatgatgtc atacttatcc   8100 tgtcccttt  ttttccacag ctcgcggttg aggacaaact cttcgcggtc tttccagtac   8160
tcttggatcg gaaacccgtc ggcctccgaa cggtaagagc ctagcatgta gaactggttg   8220
acggcctggt aggcgcagca tccctttcct acgggtagcg cgtatgcctg cgcggccttc   8280
cggagcgagg tgtgggtgag cgcaaaggtg tccctgacca tgactttgag gtactggtat   8340
ttgaagtcag tgtcgtcgca tccgccctgc tcccagagca aaaagtccgt gcgcttttg   8400 gaacgcggat ttggcagggc gaaggtgaca tcgttgaaga gtatctttcc cgcgcgaggc   8460
ataaagttgc gtgtgatgcg gaagggtccc ggcacctcgg aacggttgtt aattacctgg   8520
gcggcgagca cgatctcgtc aaagccgttg atgttgtggc ccacaatgta aagttccaag   8580
aagcgcggga tgcccttgat ggaaggcaat ttttaagtt  cctcgtaggt gagctcttca   8640
ggggagctga gcccgtgctc tgaaagggcc cagtctgcaa gatgagggtt ggaagcgacg   8700
aatgagctcc acaggtcacg ggccattagc atttgcaggt ggtcgcgaaa ggtcctaaac   8760
tggcgaccta tggccatttt ttctggggtg atgcagtaga aggtaagcgg gtcttgttcc   8820
cagcggtccc atccaaggtt cgcggctagg tctcgcgcgg cagtcactag aggctcatct   8880
ccgccgaact tcatgaccag catgaagggc acgagctgct tcccaaaggc ccccatccaa   8940
gtataggtct ctacatcgta ggtgacaaag agacgctcgg tgcgaggatg cgagccgatc   9000
gggaagaact ggatctcccg ccaccaattg gaggagtggc tattgatgtg gtgaaagtag   9060
aagtccctgc gacgggccga acactcgtgc tggcttttgt aaaaacgtgc gcagtactgg   9120
```

```
cagcggtgca cgggctgtac atcctgcacg aggttgacct gacgaccgcg cacaaggaag   9180
cagagtggga atttgagccc ctcgcctggc gggtttggct ggtggtcttc tacttcggct   9240
gcttgtcctt gaccgtctgg ctgctcgagg ggagttacgg tggatcggac caccacgccg   9300
cgcgagccca agtccagat gtccgcgcgc ggcggtcgga gcttgatgac aacatcgcgc    9360
agatgggagc tgtccatggt ctggagctcc cgcggcgtca ggtcaggcgg gagctcctgc   9420
aggtttacct cgcatagacg ggtcagggcg cgggctagat ccaggtgata cctaatttcc   9480
aggggctggt tggtggcggc gtcgatggct tgcaagaggc cgcatccccg cggcgcgact   9540
acggtaccgc gcggcgggcg gtgggccgcg ggggtgtcct tggatgatgc atctaaaagc   9600
ggtgacgcgg gcgagccccc ggaggtaggg ggggctccgg acccgccggg agaggggggca  9660 ggggcacgtc ggcgccgcgc gcgggcagga gctggtgctg cgcgcgtagg ttgctggcga   9720
acgcgacgac gcggcggttg atcctcctgaa tctggcgcct ctgcgtgaag acgacgggcc  9780
cggtgagctt gaacctgaaa gagagttcga cagaatcaat ttcggtgtcg ttgacgcgg   9840 cctggcgcaa aatctcctgc acgtctcctg agttgtcttg ataggcgatc tcggccatga   9900
actgctcgat ctcttcctcc tggagatctc cgcgtccggc tcgctccacg gtggcggcga   9960
ggtcgttgga aatgcgggcc atgagctgcg agaaggcgtt gaggcctccc tcgttccaga  10020
cgcggctgta gaccacgccc ccttcggcat cgcgggcgcg catgaccacc tgcgcgagat  10080
tgagctccac gtgccggggcg aagacggcgt agtttcgcag gcgctgaaag aggtagttga  10140
gggtggtggc ggtgtgttct gccacgaaga agtacataac ccagcgtcgc aacgtggatt  10200
cgttgatatc ccccaaggcc tcaaggcgct ccatggcctc gtagaagtcc acggcgaagt  10260
tgaaaaactg ggagttgcgc gccgacacgg ttaactcctc ctccagaaga cggatgagct  10320
cggcgacagt gtcgcgcacc tcgcgctcaa aggctacagg ggcctcttct tcttcttcaa  10380
tctcctcttc cataagggcc tccccttctt cttcttctgg cggcggtggg ggagggggga  10440
cacggcggcg acgacggcgc accggagagc ggtcgacaaa gcgctcgatc atctccccgc  10500
ggcgacggcg catggtctcg gtgacggcgc ggccgttctc gcgggggcgc agttggaaga  10560
cgccgcccgt catgtcccgg ttatgggttg gcggggggct gccatgcggc agggatacgg  10620
cgctaacgat gcatctcaac aattgttgtg taggtactcc gccgccgagg gacctgagcg  10680
agtccgcatc gaccggatcg gaaaacctct cgagaaaggc gtctaaccag tcacagtcgc  10740
aaggtaggct gagcaccgtg gcgggcggca gcgggcggcg gtcggggttg tttctggcgg  10800
aggtgctgct gatgatgtaa ttaaagtagg cggtcttgag acggcggatg gtcgacagaa  10860
gcaccatgtc cttgggtccg gcctgctgaa tgcgcaggcg gtcggccatg ccccaggctt  10920
cgttttgaca tcggcgcagg tctttgtagt agtcttgcat gagcctttct accggcactt  10980
cttcttctcc ttcctcttgt cctgcatctc ttgcatctat cgctgcggcg gcggcggagt  11040
ttggccgtag gtgcgccct cttcctccca tgcgtgtgac cccgaagccc ctcatcggct   11100
gaagcagggc taggtcggcg acaacgcgct cggctaatat ggcctgctgc acctgcgtga  11160
gggtagactg gaagtcatcc atgtccacaa agcggtggta tgcgcccgtg ttgatggtgt  11220
aagtgcagtt ggccataacg gaccagttaa cggtctggtg accggctgc gagagctcgg   11280 tgtacctgag acgcgagtaa gccctcgagt caaatacgta gtcgttgcaa gtccgcacca  11340
ggtactggta tcccaccaaa aagtgcggcg gcggctggcg gtagaggggc cagcgtaggg  11400
tggccggggc tccggggggcg agatcttcca acataaggcg atgatatccg tagatgtacc  11460
tggacatcca ggtgatgccg gcggcggtgg tggaggcgcg cggaaagtcg cggacgcggt  11520
```

```
tccagatgtt gcgcagcggc aaaaagtgct ccatggtcgg gacgctctgg ccggtcaggc    11580
gcgcgcaatc gttgacgctc tagcgtgcaa aaggagagcc tgtaagcggg cactcttccg    11640
tggtctggtg gataaaattcg caagggtatc atggcggacg accggggttc gagcccgta    11700 tccggccgtc cgccgtgatc catgcggtta ccgcccgcgt gtcgaaccca ggtgtgcgac    11760
gtcagacaac gggggagtgc tccttttggc ttccttccag gcgcggcggc tgctgcgcta    11820
gcttttttgg ccactggccg cgcgcagcgt aagcggttag gctggaaagc gaaagcatta    11880
agtggctcgc tccctgtagc cggagggtta ttttccaagg gttgagtcgc gggacccccg    11940
gttcgagtct cggaccggcc ggactgcggc gaacgggggt ttgcctcccc gtcatgcaag    12000
accccgcttg caaattcctc cggaaacagg gacgagcccc ttttttgctt ttcccagatg    12060
catccggtgc tgcggcagat gcgcccccct cctcagcagc ggcaagagca agagcagcgg    12120
cagacatgca gggcaccctc ccctcctcct accgcgtcag gaggggcgac atccgcggtt    12180
gacgcggcag cagatggtga ttacgaaccc ccgcggcgcc gggcccggca ctacctggac    12240
ttggaggagg gcgagggcct ggcgcggcta ggagcgccct ctcctgagcg gcacccaagg    12300
gtgcagctga agcgtgatac gcgtgaggcg tacgtgccgc ggcagaacct gtttcgcgac    12360
cgcgagggag aggagcccga ggagatgcgg gatcgaaagt tccacgcagg gcgcgagctg    12420
cggcatggcc tgaatcgcga gcggttgctg cgcgaggagg actttgagcc cgacgcgcga    12480
accgggatta gtcccgcgcg cgcacacgtg gcggccgccg acctggtaac cgcatacgag    12540
cagacggtga accaggagat taactttcaa aaaagcttta caaccacgt gcgtacgctt    12600 gtggcgcgcg aggaggtggc tataggactg atgcatctgt gggactttgt aagcgcgctg    12660
gagcaaaacc caaatagcaa gccgctcatg gcgcagctgt tccttatagt gcagcacagc    12720
agggacaacg aggcattcag ggatgcgctg ctaaacatag tagagcccga gggccgctgg    12780
ctgctcgatt tgataaacat cctgcagagc atagtggtgc aggagcgcag cttgagcctg    12840
gctgacaagg tggccgccat caactattcc atgcttagcc tgggcaagtt ttacgcccgc    12900
aagatatacc atccccctta cgttcccata gacaaggagg taaagatcga ggggttctac    12960
atgcgcatgg cgctgaaggt gcttaccttg agcgacgacc tgggcgttta tcgcaacgag    13020
cgcatccaca aggccgtgag cgtgagccgg cggcgcgagc tcagcgaccg cgagctgatg    13080
cacagcctgc aaagggccct ggctggcacg ggcagcggcg atagagaggc cgagtcctac    13140
tttgacgcgg gcgctgacct gcgctgggcc caagccgac gcgccctgga ggcagctggg    13200
gccggacctg ggctggcggt ggcacccgcg cgcgctggca acgtcggcgg cgtggaggaa    13260
tatgacgagg acgatgagta cgagccagag gacggcgagt actaagcggt gatgtttctg    13320
atcagatgat gcaagacgca acggacccgg cggtgcgggc ggcgctgcag agccagccgt    13380
ccggccttaa ctccacggac gactggcgcc aggtcatgga ccgcatcatg tcgctgactg    13440
cgcgcaatcc tgacgcgttc cggcagcagc cgcaggccaa ccggctctcc gcaattctgg    13500
aagcggtggt cccggcgcgc gcaaacccca cgcacgagaa ggtgctggcg atcgtaaacg    13560
cgctggccga aaacagggcc atccggcccg acgaggccgg cctggtctac gacgcgctgc    13620
ttcagcgcgt ggctcgttac aacagcggca acgtgcagac caacctggac cggctggtgg    13680
gggatgtgcg cgaggccgtg gcgcagcgtg agcgcgcgca gcagcagggc aacctgggct    13740 ccatggtttgc actaaacgcc ttcctgagta cacagcccgc caacgtgccg cggggacagg    13800
aggactacac caacttttgtg agcgcactgc ggctaatggt gactgagaca ccgcaaagtg    13860
```

```
aggtgtacca gtctgggcca gactattttt tccagaccag tagacaaggc ctgcagaccg    13920
taaacctgag ccaggctttc aaaaacttgc aggggctgtg gggggtgcgg gctcccacag    13980
gcgaccgcgc gaccgtgtct agcttgctga cgcccaactc gcgcctgttg ctgctgctaa    14040
tagcgcccct tcacggacagt ggcagcgtgt cccgggacac ataccctaggt cacttgctga   14100 cactgtaccg cgaggccata ggtcaggcgc atgtggacga gcatactttc caggagatta    14160
caagtgtcag ccgcgcgctg gggcaggagg acacgggcag cctggaggca accctaaact    14220
acctgctgac caaccggcgg cagaagatcc cctcgttgca cagtttaaac agcgaggagg    14280 agcgcattt gcgctacgtg cagcagagcg tgagccttaa cctgatgcgc gacggggtaa     14340
cgcccagcgt ggcgctggac atgaccgcgc gcaacatgga accgggcatg tatgcctcaa    14400
accggccgtt tatcaaccgc ctaatggact acttgcatcg cgcggccgcc gtgaaccccg    14460
agtatttcac caatgccatc ttgaacccgc actggctacc gccccctggt ttctacaccg    14520
ggggattcga ggtgcccgag ggtaacgatg gattcctctg ggacgacata gacgacagcg    14580
tgttttcccc gcaaccgcag accctgctag agttgcaaca gcgcgagcag gcagaggcgg    14640
cgctgcgaaa ggaaagcttc cgcaggccaa gcagcttgtc cgatctaggc gctgcggccc    14700
cgcggtcaga tgctagtagc ccatttccaa gcttgatagg gtctcttacc agcactcgca    14760
ccacccgccc gcgcctgctg ggcgaggagg agtacctaaa caactcgctg ctgcagccgc    14820
agcgcgaaaa aaacctgcct ccggcatttc ccaacaacgg gatagagagc ctagtggaca    14880
agatgagtag atggaagacg tacgcgcagg agcacaggga cgtgccaggc ccgcgcccgc    14940
ccacccgtcg tcaaaggcac gaccgtcagc ggggtctggt gtgggaggac gatgactcgg    15000
cagacgacag cagcgtcctg gatttgggag ggagtggcaa cccgtttgcg caccttcgcc    15060
ccaggctggg gagaatgttt taaaaaaaaa aaagcatgat gcaaaataaa aaactcacca    15120
aggccatggc accgagcgtt ggttttcttg tattcccctt agtatgcggc gcgcggcgat    15180
gtatgaggaa ggtcctcctc cctcctacga gagtgtggtg agcgcggcgc cagtggcggc    15240
ggcgctgggt tctcccttcg atgctcccct ggacccgccg tttgtgcctc cgcggtacct    15300
gcggcctacc gggggagaa acagcatccg ttactctgag ttggcacccc tattcgacac    15360 caccccgtgtg tacctggtgg acaacaagtc aacggatgtg gcatccctga actaccagaa    15420
cgaccacagc aactttctga ccacggtcat tcaaaacaat gactacagcc ggggagggc    15480 aagcacacag accatcaatc ttgacgaccg gtcgcactgg ggcggcgacc tgaaaaccat    15540
cctgcatacc aacatgccaa atgtgaacga gttcatgttt accaataagt ttaaggcgcg    15600
ggtgatggtg tcgcgcttgc ctactaagga caatcaggtg gagctgaaat acgagtgggt    15660
ggagttcacg ctgcccgagg gcaactactc cgagaccatg accatagacc ttatgaacaa    15720
cgcgatcgtg gagcactact gaaagtggg cagacagaac ggggttctgg aaagcgacat    15780
cggggtaaag tttgacaccc gcaacttcag actggggttt gaccccgtca ctggtcttgt    15840
catgcctggg gtatatacaa acgaagcctt ccatccagac atcattttgc tgccaggatg    15900
cggggtggac ttcacccaca gccgcctgag caacttgttg gcatccgca agcggcaacc    15960 cttccaggag ggctttagga tcacctacga tgatctggag ggtggtaaca ttcccgcact    16020
gttggatgtg gacgcctacc aggcgagctt gaaagatgac accgaacagg gcggggtgg    16080 cgcaggcggc agcaacagca gtggcagcgg cgcggaagag aactccaacg cggcagccgc    16140
ggcaatgcag ccggtggagg acatgaacga tcatgccatt cgcggcgaca cctttgccac    16200
acgggctgag gagaagcgcg ctgaggccga agcagcggcc gaagctgccg cccccgctgc    16260
```

-continued

```
gcaacccgag gtcgagaagc ctcagaagaa accggtgatc aaacccctga cagaggacag   16320
caagaaacgc agttacaacc taataagcaa tgacagcacc ttcacccagt accgcagctg   16380
gtaccttgca tacaactacg cgaccctca gaccggaatc cgctcatgga ccctgctttg    16440
cactcctgac gtaacctgcg gctcggagca ggtctactgg tcgttgccag acatgatgca   16500 agacccgtg accttccgct ccacgcgcca gatcagcaac tttccggtgg tgggcgccga    16560
gctgttgccc gtgcactcca agagcttcta caacgaccag gccgtctact cccaactcat   16620
ccgccagttt acctctctga cccacgtgtt caatcgcttt cccgagaacc agattttggc   16680
gcgcccgcca gcccccacca tcaccaccgt cagtgaaaac gttcctgctc tcacagatca   16740
cgggacgcta ccgctgcgca acagcatcgg aggagtccag cgagtgacca ttactgacgc   16800
cagacgccgc acctgcccct acgtttacaa ggccctgggc atagtctcgc cgcgcgtcct   16860
atcgagccgc acttttgag caagcatgtc catccttata tcgcccagca ataacacagg    16920
ctggggcctg cgcttcccaa gcaagatgtt tggcggggcc aagaagcgct ccgaccaaca   16980
cccagtgcgc gtgcgcgggc actaccgcgc gccctggggc gcgcacaaac gcggccgcac   17040
tgggcgcacc accgtcgatg acgccatcga cgcggtggtg gaggaggcgc gcaactacac   17100
gcccacgccg ccaccagtgt ccacagtgga cgcggccatt cagaccgtgg tgcgcggagc   17160
ccggcgctat gctaaaatga agagacggcg gaggcgcgta gcacgtcgcc accgccgccg   17220
acccggcact gccgcccaac gcgcggcggc ggccctgctt aaccgcgcac gtcgcaccgg   17280
ccgacgggcg gccatgcggg ccgctcgaag gctggccgcg ggtattgtca ctgtgccccc   17340
caggtccagg cgacgagcgg ccgccgcagc agccgcggcc attagtgcta tgactcaggg   17400 tcgcagggc aacgtgtatt gggtgcgcga ctcggttagc ggcctgcgcg tgcccgtgcg    17460
cacccgcccc ccgcgcaact agattgcaag aaaaaactac ttagactcgt actgttgtat   17520
gtatccagcg gcggcggcgc gcaacgaagc tatgtccaag cgcaaaatca agaagagat    17580 gctccaggtc atcgcgccgg agatctatgg ccccccgaag aaggaagagc aggattacaa   17640
gccccgaaag ctaaagcggg tcaaaaagaa aaagaaagat gatgatgatg aacttgacga   17700
cgaggtggaa ctgctgcacg ctaccgcgcc caggcgacgg gtacagtgga aggtcgacg    17760 cgtaaaacgt gttttgcgac ccggcaccac cgtagtcttt acgcccggtg agcgctccac   17820
ccgcacctac aagcgcgtgt atgatgaggt gtacggcgac gaggacctgc ttgagcaggc   17880
caacgagcgc ctcgggggagt ttgcctacgg aaagcggcat aaggacatgc tggcgttgcc   17940
gctggacgag ggcaacccaa cacctagcct aaagcccgta acactgcagc aggtgctgcc   18000
cgcgcttgca ccgtccgaag aaaagcgcgg cctaaagcgc gagtctggtg acttggcacc   18060
caccgtgcag ctgatggtac ccaagcgcca gcgactggaa gatgtcttgg aaaaaatgac   18120 cgtgaacct gggctggagc ccgaggtccg cgtgcggcca atcaagcagg tggcgccggg    18180
actgggcgtg cagaccgtgg acgttcagat acccactacc agtagcacca gtattgccac   18240
cgccacagag ggcatggaga cacaaacgtc cccggttgcc tcagcggtgg cggatgccgc   18300
ggtgcaggcg gtcgctgcgg ccgcgtccaa gacctctacg gaggtgcaaa cggacccgtg   18360
gatgtttcgc gtttcagccc ccggcgcccc gcgccgttcg aggaagtacg cgccgccag    18420 cgcgctactg cccgaatatg ccctacatcc ttccattgcg cctaccccg gctatcgtgg     18480 ctacacctac cgccccagaa gacgagcaac tacccgacgc cgaaccacca ctggaacccg   18540 ccgccgcccgt cgccgtcgcc agcccgtgct ggccccgatt ccgtgcgca gggtggctcg    18600
```

```
cgaaggaggc aggaccctgg tgctgccaac agcgcgctac caccccagca tcgtttaaaa   18660
gccggtcttt gtggttcttg cagatatggc cctcacctgc cgcctccgtt tcccggtgcc   18720
gggattccga ggaagaatgc accgtaggag gggcatggcc ggccacggcc tgacgggcgg   18780
catgcgtcgt gcgcaccacc ggcggcggcg cgcgtcgcac cgtcgcatgc gcggcggtat   18840
cctgcccctc cttattccac tgatcgccgg ggcgattggc gccgtgcccg gaattgcatc   18900
cgtggccttg caggcgcaga gacactgatt aaaaacaagt tgcatgtgga aaaatcaaaa   18960
taaaaagtct ggactctcac gctcgcttgg tcctgtaact attttgtaga atggaagaca   19020
tcaactttgc gtctctggcc ccgcgacacg gctcgcgccc gttcatggga aactggcaag   19080
atatcggcac cagcaatatg agcggtggcg ccttcagctg gggctcgctg tggagcggca   19140
ttaaaaattt cggttccacc gttaagaact atggcagcaa ggcctggaac agcagcacag   19200
gccagatgct gagggataag ttgaaagagc aaaatttcca acaaaaggtg gtagatggcc   19260
tggcctctgg cattagcggg gtggtggacc tggccaacca ggcagtgcaa aataagatta   19320
acagtaagct tgatccccgc cctcccgtag aggagcctcc accggccgtg gagacagtgt   19380
ctccagaggg gcgtggcgaa aagcgtccgc gccccgacag ggaagaaact ctggtgacgc   19440
aaatagacga gcctccctcg tacgaggagg cactaaagca aggcctgccc accacccgtc   19500
ccatcgcgcc catggctacc ggagtgctgg gccagcacac acccgtaacg ctggacctgc   19560 ctcccccgc cgacacccag cagaaacctg tgctgccagg cccgaccgcc gttgttgtaa   19620
cccgtcctag ccgcgcgtcc ctgcgccgcg ccgccagcgg tccgcgatcg ttgcggcccg   19680
tagccagtgg caactggcaa agcacactga acagcatcgt gggtctgggg gtgcaatccc   19740
tgaagcgccg acgatgcttc tgatagctaa cgtgtcgtat gtgtgtcatg tatgcgtcca   19800
tgtcgccgcc agaggagctg ctgagccgcc gcgcgcccgc tttccaagat ggctacccct   19860
tcgatgatgc cgcagtggtc ttacatgcac atctcgggcc aggacgcctc ggagtacctg   19920
agccccgggc tggtgcagtt tgcccgcgcc accgagacgt acttcagcct gaataacaag   19980
tttagaaacc ccacggtggc gcctacgcac gacgtgacca cagaccggtc ccagcgtttg   20040
acgctgcggt tcatccctgt ggaccgtgag gatactgcgt actcgtacaa ggcgcggttc   20100
accctagctg tgggtgataa ccgtgtgctg gacatggctt ccacgtactt tgacatccgc   20160
ggcgtgctgg acaggggccc tacttttaag ccctactctg gcactgccta caacgccctg   20220
gctcccaagg gtgccccaaa tccttgcgaa tgggatgaag ctgctactgc tcttgaaata   20280
aacctagaag aagaggacga tgacaacgaa gacgaagtag acgagcaagc tgagcagcaa   20340
aaaactcacg tatttgggca ggcgccttat tctggtataa atattacaaa ggagggtatt   20400
caaataggtg tcgaaggtca aacacctaaa tatgccgata aaacatttca acctgaacct   20460
caaataggag aatctcagtg gtacgaaaca gaaattaatc atgcagctgg gagagtccta   20520
aaaaagacta ccccaatgaa accatgttac ggttcatatg caaacccac aaatgaaaat   20580 ggagggcaag gcattcttgt aaagcaacaa aatggaaagc tagaaagtca agtggaaatg   20640 caattttct caactactga ggcagccgca ggcaatggtg ataacttgac tcctaaagtg   20700
gtattgtaca gtgaagatgt agatatagaa accccagaca ctcatatttc ttacatgccc   20760
actattaagg aaggtaactc acgagaacta atgggccaac aatctatgcc caacaggcct   20820
aattacattg cttttaggga caatttttatt ggtctaatgt attacaacag cacgggtaat   20880
atgggtgttc tggcgggcca agcatcgcag ttgaatgctg ttgtagattt gcaagacaga   20940
aacacagagc tttcatacca gcttttgctt gattccattg gtgatagaac caggtacttt   21000
```

```
tctatgtgga atcaggctgt tgacagctat gatccagatg ttagaattat tgaaaatcat   21060
ggaactgaag atgaacttcc aaattactgc tttccactgg gaggtgtgat taatacagag   21120
actcttacca aggtaaaacc taaaacaggt caggaaaatg gatgggaaaa agatgctaca   21180
gaattttcag ataaaaatga aataagagtt ggaaataatt ttgccatgga aatcaatcta   21240
aatgccaacc tgtggagaaa tttcctgtac tccaacatag cgctgtattt gcccgacaag   21300
ctaaagtaca gtccttccaa cgtaaaaatt tctgataacc aaacaccta cgactacatg    21360
aacaagcgag tggtggctcc cgggctagtg gactgctaca ttaaccttgg agcacgctgg   21420
tcccttgact atatggacaa cgtcaaccca tttaaccacc accgcaatgc tggcctgcgc   21480
taccgctcaa tgttgctggg caatggtcgc tatgtgccct tccacatcca ggtgcctcag   21540
aagttctttg ccattaaaaa cctccttctc ctgccgggct catacaccta cgagtggaac   21600
ttcaggaagg atgttaacat ggttctgcag agctccctag gaaatgacct aagggttgac   21660
ggagccagca ttaagtttga tagcatttgc ctttacgcca ccttcttccc catggcccac   21720
aacaccgcct ccacgcttga ggccatgctt agaaacgaca ccaacgacca gtcctttaac   21780
gactatctct ccgccgccaa catgctctac cctataccg ccaacgctac caacgtgccc    21840
atatccatcc cctcccgcaa ctgggcggct ttccgcggct gggccttcac gcgccttaag   21900
actaaggaaa ccccatcact gggctcgggc tacgacccct attacaccta ctctggctct   21960
atacctacc tagatggaac ctttttacctc aaccacacct ttaagaaggt ggccattacc    22020
tttgactctt ctgtcagctg gcctggcaat gaccgcctgc ttaccccaa cgagtttgaa    22080
attaagcgct cagttgacgg ggagggttac aacgttgccc agtgtaacat gaccaaagac   22140
tggttcctgg tacaaatgct agctaactat aacattggct accagggctt ctatatccca   22200
gagagctaca aggaccgcat gtactccttc tttagaaact tccagcccat gagccgtcag   22260
gtggtggatg atactaaata caaggactac caacaggtgg gcatcctaca ccaacacaac   22320
aactctggat tgttggcta ccttgccccc accatgcgcg aaggacaggc ctaccctgct    22380
aacttccct atccgcttat aggcaagacc gcagttgaca gcattaccca gaaaagttt    22440
ctttgcgatc gcacccttg gcgcatccca ttctccagta actttatgtc catgggcgca   22500
ctcacagacc tgggccaaaa ccttctctac gccaactccg cccacgcgct agacatgact   22560
tttgaggtgg atcccatgga cgagcccacc cttctttatg ttttgtttga agtctttgac   22620
gtggtccgtg tgcaccagcc gcaccgcggc gtcatcgaaa ccgtgtacct gcgcacgccc   22680
ttctcggccg gcaacgccac aacataaaga agcaagcaac atcaacaaca gctgccgcca   22740
tgggctccag tgagcaggaa ctgaaagcca ttgtcaaaga tcttggttgt gggccatatt   22800
ttttgggcac ctatgacaag cgctttccag gctttgtttc tccacacaag ctcgcctgcg   22860
ccatagtcaa tacggccggt cgcgagactg ggggcgtaca ctggatggcc tttgcctgga   22920
acccgcactc aaaaacatgc tacctctttg agcccttttgg cttttctgac cagcgactca   22980
agcaggttta ccagtttgag tacgagtcac tcctgcgccg tagcgccatt gcttcttccc   23040
ccgaccgctg tataacgctg gaaaagtcca cccaaagcgt acaggggccc aactcggccg   23100
cctgtggact attctgctgc atgtttctcc acgcctttgc caactggccc caaactccca   23160
tggatcacaa ccccaccatg aaccttatta ccggggtacc caactccatg ctcaacagtc   23220
cccaggtaca gcccacctg cgtcgcaacc aggaacagct ctacagcttc ctggagcgcc    23280
actcgcccta cttccgcagc cacagtgcgc agattaggag cgccacttct ttttgtcact   23340
```

```
tgaaaaacat gtaaaaataa tgtactagag acactttcaa taaaggcaaa tgcttttatt    23400
tgtacactct cgggtgatta tttaccccca cccttgccgt ctgcgccgtt taaaaatcaa    23460
aggggttctg ccgcgcatcg ctatgcgcca ctggcaggga cacgttgcga tactggtgtt    23520
tagtgctcca cttaaactca ggcacaacca tccgcggcag ctcggtgaag ttttcactcc    23580
acaggctgcg caccatcacc aacgcgttta gcaggtcggg cgccgatatc ttgaagtcgc    23640
agttggggcc tccgccctgc gcgcgcgagt tgcgatacac agggttgcag cactggaaca    23700
ctatcagcgc cgggtggtgc acgctggcca gcacgctctt gtcggagatc agatccgcgt    23760
ccaggtcctc cgcgttgctc agggcgaacg gagtcaactt ggtagctgc cttcccaaaa    23820 agggcgcgtg cccaggcttt gagttgcact cgcaccgtag tggcatcaaa aggtgaccgt    23880
gcccggtctg ggcgttagga tacagcgcct gcataaaagc cttgatctgc ttaaaagcca    23940
cctgagcctt tgcgccttca gagaagaaca tgccgcaaga cttgccggaa aactgattgg    24000
ccggacaggc cgcgtcgtgc acgcagcacc ttgcgtcggt gttggagatc tgcaccacat    24060
ttcggcccca ccggttcttc acgatcttgg ccttgctaga ctgctccttc agcgcgcgct    24120
gcccgttttc gctcgtcaca tccatttcaa tcacgtgctc cttatttatc ataatgcttc    24180
cgtgtagaca cttaagctcg ccttcgatct cagcgcagcg gtgcagccac aacgcgcagc    24240
ccgtgggctc gtgatgcttg taggtcacct ctgcaaacga ctgcaggtac gcctgcagga    24300
atcgccccat catcgtcaca aaggtcttgt tgctggtgaa ggtcagctgc aacccgcggt    24360
gctcctcgtt cagccaggtc ttgcatacgg ccgccagagc ttccacttgg tcaggcagta    24420
gtttgaagtt cgcctttaga tcgttatcca cgtggtactt gtccatcagc gcgcgcgcag    24480
cctccatgcc cttctcccac gcagacacga tcggcacact cagcgggttc atcaccgtaa    24540
tttcactttc cgcttcgctg ggctcttcct cttcctcttg cgtccgcata ccacgcgcca    24600
ctgggtcgtc ttcattcagc cgccgcactg tgccgcttacc tcctttgcca tgcttgatta    24660
gcaccggtgg gttgctgaaa cccaccattt gtagcgccac atcttctctt tcttcctcgc    24720
tgtccacgat tacctctggt gatggcgggc gctcggcctt gggagaaggg cgcttctttt    24780
tcttcttggg cgcaatggcc aaatccgccg ccgaggtcga tggccgcggg ctgggtgtgc    24840
gcggcaccag cgcgtcttgt gatgagtctt cctcgtcctc ggactcgata cgccgcctca    24900
tccgcttttt tgggggcgcc cggggaggcg gcggcgacgg ggacggggac gacacgtcct    24960
ccatggttgg gggacgtcgc gccgcaccgc gtccgcgctc ggggtggtt tcgcgctgct    25020 cctcttcccg actggccatt tccttctcct ataggcagaa aaagatcatg gagtcagtcg    25080
agaagaagga cagcctaacc gcccctctg agttcgccac caccgcctcc accgatgccg    25140
ccaacgcgcc taccaccttc cccgtcgagg cacccccgct tgaggaggag gaagtgatta    25200
tcgagcagga cccaggtttt gtaagcgaag acgacgagga ccgctcagta ccaacagagg    25260
ataaaaagca agaccaggac aacgcagagg caaacgagga acaagtcggg cggggggacg    25320
aaaggcatgg cgactaccta gatgtgggag acgacgtgct gttgaagcat ctgcagcgcc    25380
agtgcgccat tatctgcgac gcgttgcaag agcgcagcga tgtgcccctc gccatagcgg    25440
atgtcagcct tgcctacgaa cgccacctat tctcaccgcg cgtaccccc aaacgccaag    25500 aaaacggcac atgcgagccc aacccgcgcc tcaacttcta ccccgtattt gccgtgccag    25560
aggtgcttgc cacctatcac atcttttttcc aaaactgcaa gatacccta tcctgccgtg    25620 ccaaccgcag ccgagcggac aagcagctgg ccttgcggca gggcgctgtc atacctgata    25680
tcgcctcgct caacgaagtg ccaaaaatct ttgagggtct tggacgcgac gagaagcgcg    25740
```

-continued

```
cggcaaacgc tctgcaacag gaaaacagcg aaaatgaaag tcactctgga gtgttggtgg    25800
aactcgaggg tgacaacgcg cgcctagccg tactaaaacg cagcatcgag gtcacccact    25860
ttgcctaccc ggcacttaac ctaccccca aggtcatgag cacagtcatg agtgagctga    25920
tcgtgcgccg tgcgcagccc ctggagaggg atgcaaattt gcaagaacaa acagaggagg    25980
gcctacccgc agttggcgac gagcagctag cgcgctggct tcaaacgcgc gagcctgccg    26040
acttggagga gcgacgcaaa ctaatgatgg ccgcagtgct cgttaccgtg gagcttgagt    26100
gcatgcagcg gttctttgct gacccggaga tgcagcgcaa gctagaggaa acattgcact    26160
acacctttcg acagggctac gtacgccagg cctgcaagat ctccaacgtg gagctctgca    26220
acctggtctc ctaccttgga attttgcacg aaaaccgcct tgggcaaaac gtgcttcatt    26280
ccacgctcaa gggcgaggcg cgccgcgact acgtccgcga ctgcgtttac ttatttctat    26340
gctacacctg gcagacggcc atgggcgttt ggcagcagtg cttggaggag tgcaacctca    26400
aggagctgca gaaactgcta aagcaaaact tgaaggacct atggacggcc ttcaacgagc    26460
gctccgtggc cgcgcacctg gcggacatca ttttccccga acgcctgctt aaaaccctgc    26520
aacagggtct gccagacttc accagtcaaa gcatgttgca gaactttagg aactttatcc    26580
tagagcgctc aggaatcttg cccgccacct gctgtgcact tcctagcgac tttgtgccca    26640
ttaagtaccg cgaatgccct ccgccgcttt ggggccactg ctaccttctg cagctagcca    26700
actaccttgc ctaccactct gacataatgg aagacgtgag cggtgacggt ctactggagt    26760
gtcactgtcg ctgcaaccta tgcaccccgc accgctccct ggtttgcaat tcgcagctgc    26820
ttaacgaaag tcaaattatc ggtacctttg agctgcaggg tccctcgcct gacgaaaagt    26880
ccgcggctcc ggggttgaaa ctcactccgg ggctgtggac gtcggcttac cttcgcaaat    26940
ttgtacctga ggactaccac gcccacgaga ttaggttcta cgaagaccaa tcccgcccgc    27000
ctaatgcgga gcttaccgcc tgcgtcatta cccagggcca cattcttggc caattgcaag    27060
ccatcaacaa agcccgccaa gagtttctgc tacgaaaggg acgggggggtt tacttggacc    27120 cccagtccgg cgaggagctc aacccaatcc ccccgccgcc gcagccctat cagcagcagc    27180
cgcgggccct tgcttcccag gatggcaccc aaaaagaagc tgcagctgcc gccgccaccc    27240
acggacgagg aggaatactg ggacagtcag gcagaggagg ttttggacga ggaggaggag    27300
gacatgatgg aagactggga gagcctagac gaggaagctt ccgaggtcga agaggtgtca    27360
gacgaaacac cgtcaccctc ggtcgcattc ccctcgccgg cgcccagaa atcggcaacc    27420 ggttccagca tggctacaac ctccgctcct caggcgccgc cggcactgcc cgttcgccga    27480
cccaaccgta gatgggacac cactggaacc agggccggta agtccaagca gccgccgccg    27540
ttagcccaag agcaacaaca gcgccaaggc taccgctcat ggcgcgggca caagaacgcc    27600
atagttgctt gcttgcaaga ctgtgggggc aacatctcct tcgcccgccg ctttcttctc    27660
taccatcacg gcgtggcctt cccccgtaac atcctgcatt actaccgtca tctctacagc    27720
ccatactgca ccggcggcag cggcagcaac agcagcggcc acacagaagc aaaggcgacc    27780
ggatagcaag actctgacaa agcccaagaa atccacagcg gcggcagcag caggaggagg    27840
agcgctgcgt ctggcgccca acgaacccgt atcgacccgc gagcttagaa acaggatttt    27900
tcccactctg tatgctatat ttcaacagag caggggccaa gaacaagagc tgaaaataaa    27960
aaacaggtct ctgcgatccc tcacccgcag ctgcctgtat cacaaaagcg aagatcagct    28020
tcggcgcacg ctggaagacg cggaggctct cttcagtaaa tactgcgcgc tgactcttaa    28080
```

```
ggactagttt cgcgcccttt ctcaaattta agcgcgaaaa ctacgtcatc tccagcggcc   28140
acacccggcg ccagcacctg ttgtcagcgc cattatgagc aaggaaattc ccacgcccta   28200
catgtggagt taccagccac aaatgggact tgcggctgga gctgcccaag actactcaac   28260
ccgaataaac tacatgagcg cgggacccca catgatatcc cgggtcaacg gaatacgcgc   28320
ccaccgaaac cgaattctcc tggaacaggc ggctattacc accacacctc gtaataacct   28380
taatccccgt agttggcccg ctgccctggt gtaccaggaa agtcccgctc ccaccactgt   28440
ggtacttccc agagacgccc aggccgaagt tcagatgact aactcagggg cgcagcttgc   28500
gggcggcttt cgtcacaggg tgcggtcgcc cgggcagggt ataactcacc tgacaatcag   28560
agggcgaggt attcagctca acgacgagtc ggtgagctcc tcgcttggtc tccgtccgga   28620
cgggacattt cagatcggcg gcgccggccg ctcttcattc acgcctcgtc aggcaatcct   28680
aactctgcag acctcgtcct ctgagccgcg ctctggaggc attggaactc tgcaatttat   28740
tgaggagttt gtgccatcgg tctactttaa cccttctcg ggacctcccg ccactatcc   28800 ggatcaattt attcctaact ttgacgcggt aaaggactcg gcggacggct acgactgaat   28860
gttaagtgga gaggcagagc aactgcgcct gaaacacctg gtccactgtc gccgccacaa   28920
gtgctttgcc cgcgactccg gtgagttttg ctactttgaa ttgcccgagg atcatatcga   28980
gggcccggcg cacggcgtcc ggcttaccgc ccagggagag cttgcccgta gcctgattcg   29040
ggagtttacc cagcgccccc tgctagttga gcgggacagg ggaccctgtg ttctcactgt   29100
gatttgcaac tgtcctaacc ctggattaca tcaagatcct ctagttaata ctagtattta   29160
aataattccc tggcattatg cccagtacat gaccttatgg gactttccta cttggcagta   29220
catctacgta ttagtcatcg ctattaccat ggtgatgcgg ttttggcagt acatcaatgg   29280
gcgtggatag cggtttgact cacggggatt ccaagtctc caccccattg acgtcaatgg   29340
gagtttgttt tggcaccaaa atcaacggga ctttccaaaa tgtcgtaaca actccgcccc   29400
attgacgcaa atgggcggta ggcgtgtacg gtgggaggtc tatataagca gagctcgttt   29460
agtgaaccgt cagatcgcct ggagacgcca tccacgctgt tttgacctcc atagaagaca   29520
ccgggaccga tccagcctgg ggatcttcga gtcgagggat cccctgctcc agagatgacc   29580
ggcacaacca acgcggccgc cgctaccgga cttacatcta ccacaaatac accccaagtt   29640
tctgcctttg tcaataactg ggataacttg gcatgtggt ggttctccat agcgcttatg   29700
tttgtatgcc ttattattat gtggctcatc tgctgcctaa agcgcaaacg cgcccgacca   29760
cccatctata gtcccatcat tgtgctacac ccaaacaatg atggaatcca tagattggac   29820
ggactgaaac acatgttctt ttctcttaca gtatgattaa atgagacatg attccaagct   29880
tgtcgacttc gagcaacttg tttattgcag cttataatgg ttacaaataa agcaatagca   29940
tcacaaattt cacaaataaa gcattttttt cactgcattc tagttgtggt ttgtccaaac   30000
tcatcaatgt atcttatcat gtctggatcg tctagcattt aattaactag agtacccggg   30060
gatcttattc cctttaacta ataaaaaaaa ataataaagc atcacttact taaaatcagt   30120
tagcaaattt ctgtccagtt tattcagcag cacctccttg ccctcctccc agctctgta   30180 ttgcagcttc ctcctggctg caaactttct ccacaatcta atggaatgt cagtttcctc   30240 ctgttcctgt ccatccgcac ccactatctt catgttgttg cagatgaagc gcgcaagacc   30300
gtctgaagat accttcaacc ccgtgtatcc atatgacacg gaaaccggtc tccaactgt   30360 gccttttctt actcctccct ttgtatcccc caatggtttt caagagagtc cccctggggt   30420
actctctttg cgcctatccg aacctctagt tacctccaat ggcatgcttg cgctcaaaat   30480
```

```
gggcaacggc ctctctctgg acgaggccgg caaccttacc tcccaaaatg taaccactgt    30540
gagcccacct ctcaaaaaaa ccaagtcaaa cataaacctg aaatatctg caccccctcac    30600 agttacctca gaagcctaa ctgtggctgc cgccgcacct ctaatggtcg cgggcaacac    30660
actcaccatg caatcacagg ccccgctaac cgtgcacgac tccaaactta gcattgccac    30720
ccaaggaccc ctcacagtgt cagaaggaaa gctagccctg caaacatcag gcccctcac    30780 caccaccgat agcagtaccc ttactatcac tgcctcaccc cctctaacta ctgccactgg    30840
tagcttgggc attgacttga aagagcccat ttatacacaa aatggaaaac taggactaaa    30900
gtacggggct cctttgcatg taacagacga cctaaacact ttgaccgtag caactggtcc    30960
aggtgtgact attaataata cttccttgca aactaaagtt actggagcct tgggttttga    31020
ttcacaaggc aatatgcaac ttaatgtagc aggaggacta aggattgatt ctcaaaacag    31080 acgcctata cttgatgtta gttatccgtt tgatgctcaa aaccaactaa atctaagact    31140
aggacagggc cctcttttta taaactcagc ccacaacttg gatattaact acaacaaagg    31200
cctttacttg tttacagctt caaacaattc caaaaagctt gaggttaacc taagcactgc    31260
caaggggttg atgtttgacg ctacagccat agccattaat gcaggagatg ggcttgaatt    31320
tggttcacct aatgcaccaa acacaaatcc cctcaaaaca aaaattggcc atggcctaga    31380
atttgattca aacaaggcta tggttcctaa actaggaact ggccttagtt ttgacagcac    31440
aggtgccatt acagtaggaa acaaaaataa tgataagcta actttgtgga ccacaccagc    31500
tccatctcct aactgtagac taaatgcaga gaaagatgc aaactcactt tggtcttaac    31560
aaaatgtggc agtcaaatac ttgctacagt ttcagttttg gctgttaaag gcagtttggc    31620
tccaatatct ggaacagttc aaagtgctca tcttattata agattgacg aaaatggagt    31680 gctactaaac aattccttcc tggacccaga atattggaac tttagaaatg gagatcttac    31740
tgaaggcaca gcctatacaa acgctgttgg attatgcct aacctatcag cttatccaaa    31800
atctcacggt aaaactgcca aaagtaacat tgtcagtcaa gtttacttaa acggagacaa    31860
aactaaacct gtaacactaa ccattacact aaacggtaca caggaaacag agacacaac    31920 tccaagtgca tactctatgt cattttcatg ggactggtct ggccacaact acattaatga    31980
aatatttgcc acatcctctt cacttttttc atacattgcc caagaataaa gaatcgtttg    32040
tgttatgttt caacgtgttt attttttcaat tgcagaaaat ttcaagtcat tttttcattca    32100 gtagtatagc cccaccacca catagcttat acagatcacc gtaccttaat caaactcaca    32160 gaacccctagt attcaaacctg ccacctccct cccaacacac agagtacaca gtcctttctc    32220
cccggctggc cttaaaaagc atcatatcat gggtaacaga catattctta ggtgttatat    32280
tccacacggt ttcctgtcga gccaaacgct catcagtgat attaataaac tccccgggca    32340
gctcacttaa gttcatgtcg ctgtccagct gctgagccac aggctgctgt ccaacttgcg    32400
gttgcttaac gggcggcgaa ggagaagtcc acgcctacat gggggtagag tcataatcgt    32460
gcatcaggat agggcggtgg tgctgcagca gcgcgcgaat aaactgctgc cgccgccgct    32520
ccgtcctgca ggaatacaac atggcagtgg tctcctcagc gatgattcgc accgcccgca    32580
gcataaggcg ccttgtcctc cgggcacagc agcgcaccct gatctcactt aaatcagcac    32640
agtaactgca gcacagcacc acaatattgt tcaaaatccc acagtgcaag gcgctgtatc    32700
caaagctcat ggcggggacc acagaaccca cgtggccatc ataccacaag cgcaggtaga    32760
ttaagtggcg acccctcata aacacgctgg acataaacat tacctctttt ggcatgttgt    32820
```

```
aattcaccac ctcccggtac catataaacc tctgattaaa catggcgcca tccaccacca    32880
tcctaaacca gctggccaaa acctgcccgc cggctataca ctgcagggaa ccgggactgg    32940
aacaatgaca gtggagagcc caggactcgt aaccatggat catcatgctc gtcatgatat    33000
caatgttggc acaacacagg cacacgtgca tacacttcct caggattaca agctcctccc    33060
gcgttagaac catatcccag ggaacaaccc attcctgaat cagcgtaaat cccacactgc    33120
agggaagacc tcgcacgtaa ctcacgttgt gcattgtcaa agtgttacat tcgggcagca    33180
gcggatgatc ctccagtatg gtagcgcggg tttctgtctc aaaggaggt agacgatccc     33240 tactgtacgg agtgcgccga gacaaccgag atcgtgttgg tcgtagtgtc atgccaaatg    33300
gaacgccgga cgtagtcata tttcctgaag caaaccagg tgcgggcgtg acaaacagat     33360
ctgcgtctcc ggtctcgccg cttagatcgc tctgtgtagt agttgtagta tatccactct    33420
ctcaaagcat ccaggcgccc cctggcttcg ggttctatgt aaactccttc atgcgccgct    33480
gccctgataa catccaccac cgcagaataa gccacaccca gccaacctac acattcgttc    33540
tgcgagtcac acacgggagg agcgggaaga gctggaagaa ccatgttttt tttttttattc    33600 caaaagatta tccaaaacct caaaatgaag atctattaag tgaacgcgct ccctccggt     33660 ggcgtggtca aactctacag ccaaagaaca gataatggca tttgtaagat gttgcacaat    33720
ggcttccaaa aggcaaacgg ccctcacgtc caagtggacg taaaggctaa acccttcagg    33780
gtgaatctcc tctataaaca ttccagcacc ttcaaccatg cccaaataat tctcatctcg    33840
ccaccttctc aatatatctc taagcaaatc ccgaatatta agtccggcca ttgtaaaaat    33900
ctgctccaga gcgccctcca ccttcagcct caagcagcga atcatgattg caaaaattca    33960
ggttcctcac agacctgtat aagattcaaa agcggaacat taacaaaaat accgcgatcc    34020
cgtaggtccc ttcgcagggc cagctgaaca taatcgtgca ggtctgcacg gaccagcgcg    34080
gccacttccc cgccaggaac catgacaaaa gaacccacac tgattatgac acgcatactc    34140
ggagctatgc taaccagcgt agccccgatg taagcttgtt gcatgggcgg cgatataaaa    34200
tgcaaggtgc tgctcaaaaa atcaggcaaa gcctcgcgca aaaagaaag cacatcgtag     34260 tcatgctcat gcagataaag gcaggtaagc tccggaacca ccacagaaaa agacaccatt    34320
tttctctcaa acatgtctgc gggtttctgc ataaacacaa aataaaataa caaaaaaaca    34380
tttaaacatt agaagcctgt cttacaacag gaaaaacaac ccttataagc ataagacgga    34440
ctacggccat gccggcgtga ccgtaaaaaa actggtcacc gtgattaaaa agcaccaccg    34500
acagctcctc ggtcatgtcc ggagtcataa tgtaagactc ggtaaacaca tcaggttgat    34560
tcacatcggt cagtgctaaa aagcgaccga aatagcccgg gggaatacat acccgcaggc    34620
gtagagacaa cattacagcc cccataggag gtataacaaa attaatagga gagaaaaaca    34680
cataaacacc tgaaaaaccc tcctgcctag gcaaaatagc accctcccgc tccagaacaa    34740
catacagcgc ttcacagcg gcagccataa cagtcagcct taccagtaaa aagaaaacc      34800 tattaaaaaa acaccactcg acacggcacc agctcaatca gtcacagtgt aaaaaagggc    34860
caagtgcaga gcgagtatat ataggactaa aaaatgacgt aacggttaaa gtccacaaaa    34920
aacacccaga aaccgcacg cgaacctacg cccagaaacg aaagccaaaa aacccacaac     34980
ttcctcaaat cgtcacttcc gttttcccac gttacgtcac ttcccatttt aagaaaacta    35040
caattcccaa cacatacaag ttactccgcc ctaaaaccta cgtcacccgc cccgttccca    35100
cgccccgcgc cacgtcacaa actccacccc ctcattatca tattggcttc aatccaaaat    35160
aaggtatatt attgatgatg                                               35180
```

<210> SEQ ID NO 2
<211> LENGTH: 5100
<212> TYPE: DNA
<213> ORGANISM: Adenovirus

<400> SEQUENCE: 2

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tctctagcat cgaagatcca     360
tttgtctagg gccgcgggga cttgaccgt ttacgtggag actcgcccag gtgttttct     420
caggtgtttt ccgcgttccg ggtcaaagtt ggcgttttat tattatagtc agctgacgtg     480
tagtgtattt atacccggtg agttcctcaa gaggccactc ttgagtgcca gcagtagag     540
ttttctcctc cgagccgctc cgacaccggg actgaaaatg agacatatta tctgccacgg     600
aggtgttatt accgaagaaa tggccgccag tcttttggac cagctgatcg aagaggtact     660
ggctgataat cttccacctc ctagccattt tgaaccacct acccttcacg aactgtatga     720
tttagacgtg acggccccg aagatcccaa cgaggaggcg cttcgcaga ttttccccga     780
ctctgtaatg ttggcggtgc aggaagggat tgacttactc acttttccgc cggcgcccgg     840
ttctccggag ccgcctcacc tttccggca gcccgagcag ccggagcaga gagccttggg     900
tccggtttct atgccaaacc ttgtaccgga ggtgatcgat cttacctgcc acgaggctgg     960
ctttccaccc agtgacgacg aggatgaaga gggtgaggag tttgtgttag attatgtgga    1020
gcaccccggg cacggttgca ggtcttgtca ttatcaccgg aggaatacgg gggacccaga    1080
tattatgtgt tcgctttgct atatgaggac ctgtggcatg tttgtctaca gtaagtgaaa    1140
attatgggca gtgggtgata gagtggtggg tttggtgtgg taatttttt tttaattttt    1200
acagttttgt ggtttaaaga attttgtatt gtgatttttt taaaaggtcc tgtgtctgaa    1260
cctgagcctg agcccgagcc agaaccggag cctgcaagac ctaccgccg tcctaaaatg    1320
gcgcctgcta tcctgagacg cccgacatca cctgtgtcta gagaatgcaa tagtagtacg    1380
gatagctgtg actccggtcc ttctaacaca cctcctgaga tacacccggt ggtcccgctg    1440
tgccccatta aaccagttgc cgtgagagtt ggtgggcgtc gccaggctgt ggaatgtatc    1500
gaggacttgc ttaacgagcc tgggcaacct ttggacttga gctgtaaacg ccccaggcca    1560
taaggtgtaa acctgtgatt gcgtgtgtgg ttaacgcctt tgtttgctga atgagttgat    1620
gtaagtttaa taagggtga gataatgttt aacttgcatg gcgtgttaaa tggggcgggg    1680
cttaaagggt atataatgcg ccgtgggcta atcttggtta catctgacct catggaggct    1740
tgggagtgtt tggaagattt ttctgctgtg cgtaacttgc tggaacagag ctctaacagt    1800
acctcttggt tttggaggtt tctgtggggc tcatcccagg caaagttagt ctgcagaatt    1860
aaggaggatt acaagtggga atttgaagag cttttgaaat cctgtggtga gctgtttgat    1920
tctttgaatc tgggtcacca ggcgcttttc caagagaagg tcatcaagac tttggatttt    1980
tccacaccgg ggcgcgctgc ggctgctgtt gcttttttga gttttataaa ggataaatgg    2040
agcgaagaaa cccatctgag cggggggtac ctgctggatt ttctggccat gcatctgtgg    2100
```

-continued

```
agagcggttg tgagacacaa gaatcgcctg ctactgttgt cttccgtccg cccggcgata    2160
ataccgacgg aggagcagca gcagcagcag gaggaagcca ggcggcggcg gcaggagcag    2220
agcccatgga acccgagagc cggcctggac cctcgggaat gaatgttgta taggtggctt    2280
aactgtatag atctaattcc ctggcattat gcccagtaca tgaccttatg ggactttcct    2340
acttggcagt acatctacgt attagtcatc gctattacca tggtgatgcg gttttggcag    2400
tacatcaatg ggcgtggata gcggtttgac tcacggggat ttccaagtct ccaccccatt    2460
gacgtcaatg ggagtttgtt ttggcaccaa aatcaacggg actttccaaa atgtcgtaac    2520
aactccgccc cattgacgca aatgggcggt aggcgtgtac ggtgggaggt ctatataagc    2580
agagctcgtt tagtgaaccg tcagatcgcc tggagacgcc atccacgctg ttttgacctc    2640
catagaagac accgggaccg atccagcctg gggatcttcg agtcgaggga tccctcgagc    2700
caccatggtg acaggggaa tggcaagcaa gtgggatcag aagggtatgg acgttgccta    2760
tgaggaggcg gccttaggtt acaaagaggg tggtgttcct attggcggat gtcttatcaa    2820
taacaaagac ggaagtgttc tcggtcgtgg tcacaacatg agatttcaaa agggatccgc    2880
cacactacat ggtgagatct ccactttgga aaactgtggg agattagagg caaagtgta    2940 caaagatacc actttgtata cgacgctgtc tccatgcgac atgtgtacag gtgccatcat    3000
catgtatggt attccacgct gtgttgtcgg tgagaacgtt aatttcaaaa gtaagggcga    3060
gaaatattta caaactagag gtcacgaagt tgttgttgtt gacgatgaga ggtgtaaaaa    3120
gatcatgaaa caatttatcg atgaaagacc tcaggattgg tttgaagata ttggtgaggg    3180
tggaggggga ggcggtgggg gaggtgctag catggcttcg taccccggcc atcaacacgc    3240
gtctgcgttc gaccaggctg cgcgttctcg cggccatagc aaccgacgta cggcgttgcg    3300
ccctcgccgg cagcaagaag ccacggaagt ccgcccggag cagaaaatgc ccacgctact    3360
gcgggtttat atagacggtc cccacgggat ggggaaaacc accaccacgc aactgctggt    3420
ggccctgggt tcgcgcgacg atatcgtcta cgtacccgag ccgatgactt actggcgggt    3480
gctgggggct tccgagacaa tcgcgaacat ctacaccaca caacaccgcc tcgaccaggg    3540
tgagatatcg gccggggacg cggcggtggt aatgacaagc gcccagataa caatgggcat    3600
gccttatgcc gtgaccgacg ccgttctggc tcctcatatc gggggggagg ctgggagctc    3660
acatgccccg ccccggccc tcaccatctt cctcgaccgc catcccatcg ccttcatgct    3720
gtgctacccg gccgcgcggt accttatggg cagcatgacc ccccaggccg tgctggcgtt    3780
cgtggccctc atcccgccga ccttgcccgg caccaacatc gtgcttgggg cccttccgga    3840
ggacagacac atcgaccgcc tggccaaacg ccagcgcccc ggcgagcggc tggacctggc    3900
tatgctggct gcgattcgcc gcgtttacgg gctacttgcc aatacggtgc ggtatctgca    3960
gtgcggcggg tcgtggcggg aggactgggg acagctttcg gggacggccg tgccgcccca    4020
gggtgccgag ccccagagca acgcggggcc acgaccccat atcggggaca cgttatttac    4080
cctgtttcgg gccccgagt tgctggcccc caacggcgac ctgtataacg tgtttgcctg    4140
ggccttggac gtcttggcca aacgcctccg ttccatgcac gtctttatcc tggattacga    4200
ccaatcgccc gccggctgcc gggacgccct gctgcaactt acctccggga tggtccagac    4260
ccacgtcacc acccccggct ccataccgac gatatgcgac ctggcgcgca cgtttgcccg    4320
ggagatgggg gaggctaact gaaacacgga agaattcaag cttgtcgact tcgagcaact    4380
tgtttattgc agcttataat ggttacaaat aaagcaatag catcacaaat ttcacaaata    4440
aagcattttt ttcactgcat tctagttgtg gtttgtccaa actcatcaat gtatcttatc    4500
```

```
atgtctggat cgtctagcat cgaagatctg gatctgggcg tggttaaggg tgggaaagaa    4560
tatataaggt gggggtctta tgtagttttg tatctgtttt gcagcagccg ccgccgccat    4620
gagcaccaac tcgtttgatg aagcattgt gagctcatat ttgacaacgc gcatgccccc    4680
atgggccggg gtgcgtcaga atgtgatggg ctccagcatt gatggtcgcc ccgtcctgcc    4740
cgcaaactct actaccttga cctacgagac cgtgtctgga acgccgttgg agactgcagc    4800
ctccgccgcc gcttcagccg ctgcagccac cgcccgcggg attgtgactg actttgcttt    4860
cctgagcccg cttgcaagca gtgcagcttc ccgttcatcc gcccgcgatg acaagttgac    4920
ggctcttttg gcacaattgg attctttgac ccgggaactt aatgtcgttt ctcagcagct    4980
gttggatctg cgccagcagg tttctgccct gaaggcttcc tcccctccca atgcggttta    5040
aaacataaat aaaaaaccag actctgtttg gatttggatc aagcaagtgt cttgctgtct    5100
```

<210> SEQ ID NO 3
<211> LENGTH: 890
<212> TYPE: DNA
<213> ORGANISM: Adenovirus

<400> SEQUENCE: 3

```
atttaaataa ttccctggca ttatgcccag tacatgacct tatgggactt tcctacttgg     60
cagtacatct acgtattagt catcgctatt accatggtga tgcggttttg gcagtacatc    120
aatgggcgtg gatagcggtt tgactcacgg ggatttccaa gtctccaccc cattgacgtc    180
aatgggagtt tgttttggca ccaaaatcaa cgggactttc caaaatgtcg taacaactcc    240
gccccattga cgcaaatggg cggtaggcgt gtacggtggg aggtctatat aagcagagct    300
cgtttagtga accgtcagat cgcctggaga cgccatccac gctgttttga cctccataga    360
agacaccggg accgatccag cctggggatc ttcgagtcga gggatcccct gctccagaga    420
tgaccggcac aaccaacgcg gccgccgcta ccggacttac atctaccaca aatacacccc    480
aagtttctgc ctttgtcaat aactgggata acttgggcat gtggtggttc tccatagcgc    540
ttatgtttgt atgccttatt attatgtggc tcatctgctg cctaaagcgc aaacgcgccc    600
gaccacccat ctatagtccc atcattgtgc tacacccaaa caatgatgga atccatagat    660
tggacggact gaaacacatg ttcttttctc ttacagtatg attaaatgag acatgattcc    720
aagcttgtcg acttcgagca acttgtttat tgcagcttat aatggttaca aataaagcaa    780
tagcatcaca aatttcacaa taaagcattt ttttcactgc attctagttg tggtttgtcc    840
aaactcatca atgtatctta tcatgtctgg atcgtctagc atttaattaa                890
```

<210> SEQ ID NO 4
<211> LENGTH: 1635
<212> TYPE: DNA
<213> ORGANISM: Adenovirus

<400> SEQUENCE: 4

```
atggtgacag ggggaatggc aagcaagtgg gatcagaagg gtatggacgt tgcctatgag     60
gaggcggcct taggttacaa agagggtggt gttcctattg gcggatgtct tatcaataac    120
aaagacggaa gtgttctcgg tcgtggtcac aacatgagat tcaaaagggg atccgccaca    180
ctacatggtg agatctccac tttggaaaac tgtgggagat tagagggcaa agtgtacaaa    240
gataccactt tgtatacgac gctgtctcca tgcgacatgt gtacaggtgc catcatcatg    300
tatggtattc cacgctgtgt tgtcggtgag aacgttaatt tcaaaagtaa gggcgagaaa    360
```

```
tatttacaaa ctagaggtca cgaagttgtt gttgttgacg atgagaggtg taaaaagatc      420
atgaaacaat ttatcgatga aagacctcag gattggtttg aagatattgg tgagggtgga      480
gggggaggcg gtgggggagg tgctagcatg gcttcgtacc ccggccatca acacgcgtct      540
gcgttcgacc aggctgcgcg ttctcgcggc catagcaacc gacgtacggc gttgcgccct      600
cgccggcagc aagaagccac ggaagtccgc ccggagcaga aaatgccac gctactgcgg       660 gtttatatag acggtcccca cgggatgggg aaaaccacca ccacgcaact gctggtggcc      720
ctgggttcgc gcgacgatat cgtctacgta cccgagccga tgacttactg gcgggtgctg      780
ggggcttccg agacaatcgc gaacatctac accacacaac accgcctcga ccagggtgag      840
atatcggccg gggacgcggc ggtggtaatg acaagcgccc agataacaat gggcatgcct      900
tatgccgtga ccgacgccgt tctggctcct catatcgggg gggaggctgg gagctcacat      960
gccccgcccc cggccctcac catcttcctc gaccgccatc ccatcgcctt catgctgtgc     1020
tacccggccg cgcggtacct tatgggcagc atgaccccc aggccgtgct ggcgttcgtg      1080
gccctcatcc cgccgacctt gcccggcacc aacatcgtgc ttggggccct tccggaggac     1140
agacacatcg accgcctggc caaacgccag cgccccggcg agcggctgga cctggctatg     1200
ctggctgcga ttcgccgcgt ttacgggcta cttgccaata cggtgcggta tctgcagtgc     1260
ggcgggtcgt ggcgggagga ctggggacag ctttcgggga cggccgtgcc gccccagggt     1320
gccgagcccc agagcaacgc gggcccacga ccccatatcg gggacacgtt atttaccctg     1380
tttcgggccc ccgagttgct ggcccccaac ggcgacctgt ataacgtgtt tgcctgggcc     1440
ttggacgtct tggccaaacg cctccgttcc atgcacgtct ttatcctgga ttacgaccaa     1500
tcgcccgccg gctgccggga cgccctgctg caacttacct ccgggatggt ccagacccac     1560
gtcaccaccc ccggctccat accgacgata tgcgacctgg cgcgcacgtt tgcccgggag     1620 atggggagg ctaac                                                       1635

<210> SEQ ID NO 5
<211> LENGTH: 282
<212> TYPE: DNA
<213> ORGANISM: Adenovirus

<400> SEQUENCE: 5
atgaccggca caaccaacgc ggccgccgct accggactta catctaccac aaatacaccc       60
caagtttctg cctttgtcaa taactgggat aacttgggca tgtggtggtt ctccatagcg      120
cttatgtttg tatgccttat tattatgtgg ctcatctgct gcctaaagcg caaacgcgcc      180
cgaccaccca tctatagtcc catcattgtg ctacacccaa acaatgatgg aatccataga      240
ttggacggac tgaaacacat gttctttcct cttacagtat ga                        282

<210> SEQ ID NO 6
<211> LENGTH: 545
<212> TYPE: PRT
<213> ORGANISM: Adenovirus

<400> SEQUENCE: 6

Met Gly Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45
```

```
Gly His Asn Met Arg Phe Gln Lys Gly Ser Ala Thr Leu His Gly Glu
    50                  55                  60
Ile Ser Thr Leu Glu Asn Cys Gly Arg Leu Glu Gly Lys Val Tyr Lys
65                  70                  75                  80
Asp Thr Thr Leu Tyr Thr Thr Leu Ser Pro Cys Asp Met Cys Thr Gly
                    85                  90                  95
Ala Ile Ile Met Tyr Gly Ile Pro Arg Cys Val Val Gly Glu Asn Val
                100                 105                 110
Asn Phe Lys Ser Lys Gly Glu Lys Tyr Leu Gln Thr Arg Gly His Glu
            115                 120                 125
Val Val Val Asp Asp Glu Arg Cys Lys Lys Ile Met Lys Gln Phe
    130                 135                 140
Ile Asp Glu Arg Pro Gln Asp Trp Phe Glu Asp Ile Gly Glu Gly Gly
145                 150                 155                 160
Gly Gly Gly Gly Gly Gly Ala Ser Met Ala Ser Tyr Pro Cys His
                165                 170                 175
Gln His Ala Ser Ala Phe Asp Gln Ala Ala Arg Ser Arg Gly His Ser
                180                 185                 190
Asn Arg Arg Thr Ala Leu Arg Pro Arg Gln Gln Glu Ala Thr Glu
            195                 200                 205
Val Arg Leu Glu Gln Lys Met Pro Thr Leu Leu Arg Val Tyr Ile Asp
    210                 215                 220
Gly Pro His Gly Met Gly Lys Thr Thr Thr Thr Gln Leu Leu Val Ala
225                 230                 235                 240
Leu Gly Ser Arg Asp Asp Ile Val Tyr Val Pro Glu Pro Met Thr Thr
                245                 250                 255
Trp Gln Val Leu Gly Ala Ser Glu Thr Ile Ala Asn Ile Tyr Thr Thr
                260                 265                 270
Gln His Arg Leu Asp Gln Gly Glu Ile Ser Ala Gly Asp Ala Ala Val
            275                 280                 285
Val Met Thr Ser Ala Gln Ile Thr Met Gly Met Pro Tyr Ala Val Thr
    290                 295                 300
Asp Ala Val Leu Ala Pro His Val Gly Gly Glu Ala Gly Ser Ser His
305                 310                 315                 320
Ala Pro Pro Pro Ala Leu Thr Ile Phe Leu Asp Arg His Pro Ile Ala
                325                 330                 335
Phe Met Leu Cys Tyr Pro Ala Ala Arg Tyr Leu Met Gly Ser Met Thr
                340                 345                 350
Pro Gln Ala Val Leu Ala Phe Val Ala Leu Ile Pro Pro Thr Leu Pro
            355                 360                 365
Gly Thr Asn Ile Val Leu Gly Ala Leu Pro Glu Asp Arg His Ile Asp
    370                 375                 380
Arg Leu Ala Lys Arg Gln Arg Pro Gly Glu Arg Leu Asp Leu Ala Met
385                 390                 395                 400
Leu Ala Ala Ile Arg Arg Val Tyr Gly Leu Leu Ala Asn Thr Val Arg
                405                 410                 415
Tyr Leu Gln Gly Gly Gly Ser Trp Trp Glu Asp Trp Gln Leu Ser
                420                 425                 430
Gly Thr Ala Val Pro Pro Gln Gly Ala Glu Pro Gln Ser Asn Ala Gly
            435                 440                 445
Pro Arg Pro His Ile Gly Asp Thr Leu Phe Thr Leu Phe Arg Ala Pro
    450                 455                 460
Glu Leu Leu Ala Pro Asn Gly Asp Leu Tyr Asn Val Phe Ala Trp Ala
```

-continued

```
                465                 470                 475                 480
Leu Asp Val Leu Ala Lys Arg Leu Arg Pro Met His Val Phe Ile Leu
                    485                 490                 495

Asp Tyr Asp Gln Ser Pro Ala Gly Cys Arg Asp Ala Leu Leu Gln Leu
                500                 505                 510

Thr Ser Gly Met Val Gln Thr His Val Thr Thr Pro Gly Ser Ile Pro
            515                 520                 525

Thr Ile Cys Asp Leu Ala Arg Thr Phe Ala Arg Glu Met Gly Glu Ala
        530                 535                 540

Asn
545

<210> SEQ ID NO 7
<211> LENGTH: 101
<212> TYPE: PRT
<213> ORGANISM: Adenovirus

<400> SEQUENCE: 7

Met Thr Gly Ser Thr Ile Ala Pro Thr Thr Asp Tyr Arg Asn Thr Thr
1               5                   10                  15

Ala Thr Gly Leu Thr Ser Ala Leu Asn Leu Pro Gln Val His Ala Phe
            20                  25                  30

Val Asn Asp Trp Ala Ser Leu Asp Met Trp Trp Phe Ser Ile Ala Leu
        35                  40                  45

Met Phe Val Cys Leu Ile Ile Met Trp Leu Ile Cys Cys Leu Lys Arg
    50                  55                  60

Arg Arg Ala Arg Pro Pro Ile Tyr Arg Pro Ile Ile Val Leu Asn Pro
65                  70                  75                  80

His Asn Glu Lys Ile His Arg Leu Asp Gly Leu Lys Pro Cys Ser Leu
                85                  90                  95

Leu Leu Gln Tyr Asp
            100

<210> SEQ ID NO 8
<211> LENGTH: 43
<212> TYPE: DNA
<213> ORGANISM: Artificial Sequence
<220> FEATURE:
<223> OTHER INFORMATION: DNA Primer

<400> SEQUENCE: 8
gatcggatcc ctcgagatcg ctagcatggc ttcgtacccc ggc                    43

<210> SEQ ID NO 9
<211> LENGTH: 31
<212> TYPE: DNA
<213> ORGANISM: Adenovirus

<400> SEQUENCE: 9
gatcgaattc ttccgtgttt cagttagcct c                                 31

<210> SEQ ID NO 10
<211> LENGTH: 33
<212> TYPE: DNA
<213> ORGANISM: Artificial Sequence
<220> FEATURE:
<223> OTHER INFORMATION: DNA Primer

<400> SEQUENCE: 10
gatcctcgag ccaccatggt gacaggggga atg                               33
```

```
<210> SEQ ID NO 11
<211> LENGTH: 52
<212> TYPE: DNA
<213> ORGANISM: Artificial Sequence
<220> FEATURE:
<223> OTHER INFORMATION: DNA Primer

<400> SEQUENCE: 11
gatcgctagc acctccccca ccgcctctcc ctccaccctc accaatatct tc          52

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
gatcggatcc cctgctccag agatgaccgg c                                 31

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
gatcaagctt ggaatcatgt ctcamaatc                                    29

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
gatcatttaa ataattccct ggcattatgc ccagta                            36

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
gatcttaatt aatcgatgct agacgatcca gacatg                            36
```